(12) United States Patent
Stapleford et al.

(10) Patent No.: US 11,122,394 B2
(45) Date of Patent: Sep. 14, 2021

(54) AUTOMATED EXTERNAL DEFIBRILLATOR (AED) MONITORING SERVICE

(71) Applicant: Pica Product Development, LLC, Derry, NH (US)

(72) Inventors: Scott Stapleford, Londonderry, NH (US); Richard Shevelow, Estero, FL (US)

(73) Assignee: PICA Product Development, LLC, Derry, NH (US)

( * ) Notice: Subject to any disclaimer, the term of this patent is extended or adjusted under 35 U.S.C. 154(b) by 76 days.

(21) Appl. No.: 16/854,891

(22) Filed: Apr. 21, 2020

(65) Prior Publication Data

US 2020/0267509 A1    Aug. 20, 2020

Related U.S. Application Data

(63) Continuation of application No. 16/183,732, filed on Nov. 8, 2018, now Pat. No. 10,694,338.
(Continued)

(51) Int. Cl.
*H04W 4/029* (2018.01)
*A61N 1/39* (2006.01)
(Continued)

(52) U.S. Cl.
CPC .......... *H04W 4/029* (2018.02); *A61N 1/3904* (2017.08); *H04W 4/20* (2013.01); *H04W 4/90* (2018.02); *H04W 84/042* (2013.01)

(58) Field of Classification Search
CPC ......... H04W 4/029; H04W 4/20; H04W 4/90; H04W 84/042; A61N 1/3904
(Continued)

(56) References Cited

U.S. PATENT DOCUMENTS 5,671,362 A    9/1997 Cowe et al.
6,011,967 A    1/2000 Wieck
(Continued)

FOREIGN PATENT DOCUMENTS

CA    2619212 A1    9/2008
CA    2814940 A1    4/2012
(Continued)

OTHER PUBLICATIONS

Lloret et al., "A Wireless Sensor Network Deployment for Rural and Forest Fire Detection and Verification", Sensors 2009, Oct. 30, 2009, pp. 8722-8747, vol. 9, MDPI AG, Basel, Switzerland.
(Continued)

*Primary Examiner* — Farid Seyedvosoghi

(57) ABSTRACT

An automated external defibrillator (AED) monitoring service receives through a network communication from a remote AED monitoring device that senses conditions at a remote AED. The AED monitoring service receives alert messages from the remote AED monitoring device which alert the AED monitoring service to detection of sensed condition events at the remote AED. The AED monitoring service may send to designated notification recipients a notification message indicating occurrence of the sensed event at the monitored remote AED. The AED monitoring service communicates with the remote AED monitoring device only upon initiation of communications by the remote AED monitoring device, and upon initiation may request data from, or send data or control information to, the remote AED monitoring device. At the end of the communications sequence, the AED monitoring service signals the remote AED monitoring device to place itself into a low-power mode.

23 Claims, 15 Drawing Sheets

Related U.S. Application Data

(60) Provisional application No. 62/752,284, filed on Oct. 29, 2018, provisional application No. 62/582,508, filed on Nov. 7, 2017.

(51) Int. Cl.
  *H04W 4/20* (2018.01)
  *H04W 4/90* (2018.01)
  *H04W 84/04* (2009.01)

(58) Field of Classification Search
  USPC .......................................... 455/456.1; 348/143
  See application file for complete search history.

(56) References Cited

U.S. PATENT DOCUMENTS

| | | |
|---|---|---|
| 6,281,799 B1 | 8/2001 | Lake et al. |
| 6,291,568 B1 | 9/2001 | Lussey |
| 6,313,748 B1 | 11/2001 | Lake |
| 6,415,544 B1 | 7/2002 | Leyerle et al. |
| 6,445,301 B1 | 9/2002 | Farrell et al. |
| 6,508,031 B1 | 1/2003 | Johnson et al. |
| 6,574,912 B1 | 6/2003 | Johnson |
| 6,792,395 B2 | 9/2004 | Roberts |
| 6,864,789 B2 | 3/2005 | Wolfe |
| 6,914,529 B2 | 7/2005 | Barber et al. |
| 6,937,156 B2 | 8/2005 | Gardner, Jr. et al. |
| 7,002,481 B1 | 2/2006 | Crane et al. |
| 7,026,942 B2 | 4/2006 | Cristofori et al. |
| 7,076,211 B2 | 7/2006 | Donner et al. |
| 7,212,129 B2 | 5/2007 | Barber et al. |
| 7,233,781 B2 | 6/2007 | Hunter et al. |
| 7,262,702 B2 | 8/2007 | Barber et al. |
| 7,342,504 B2 | 3/2008 | Crane et al. |
| 7,626,508 B2 | 12/2009 | Kosuge et al. |
| 7,656,300 B2 | 2/2010 | Rønnau |
| 7,715,887 B2 | 5/2010 | Cloutier et al. |
| 7,768,413 B2 | 8/2010 | Kosuge et al. |
| 7,952,485 B2 | 5/2011 | Schechter et al. |
| 8,378,789 B2 | 2/2013 | Moore |
| 8,412,147 B2 | 4/2013 | Hunter et al. |
| 8,520,589 B2 | 8/2013 | Bhatt et al. |
| 8,599,010 B2 | 12/2013 | Bose et al. |
| 8,646,204 B2 | 2/2014 | Chiu |
| 8,676,377 B2 | 3/2014 | Siegel et al. |
| 8,711,785 B2 | 4/2014 | Gholmieh et al. |
| 8,797,168 B2 | 8/2014 | Tolley et al. |
| 8,830,071 B2 | 9/2014 | Borth et al. |
| 9,015,987 B2 | 4/2015 | Moran et al. |
| 9,026,147 B2 | 5/2015 | Galvin et al. |
| 9,070,268 B2 | 6/2015 | Monacos et al. |
| 9,159,211 B2 | 10/2015 | O'Brien et al. |
| 9,196,148 B1 | 11/2015 | Hutz |
| 9,226,481 B1 | 1/2016 | Paripati |
| 9,265,001 B1 * | 2/2016 | Tannenbaum ........ H04W 48/16 |
| 9,341,014 B2 | 5/2016 | Oshima et al. |
| 9,380,775 B2 | 7/2016 | Frojmovics |
| 9,439,412 B2 | 9/2016 | Kittelson |
| 9,439,995 B2 | 9/2016 | Conroy et al. |
| 9,442,594 B2 | 9/2016 | Graham et al. |
| 9,460,448 B2 | 10/2016 | Felgate |
| 9,510,582 B2 | 12/2016 | David et al. |
| 9,534,958 B1 | 1/2017 | Lhamon et al. |
| 9,542,835 B2 | 1/2017 | Borth et al. |
| 9,547,973 B1 | 1/2017 | Hutz |
| 9,613,521 B2 | 4/2017 | Hunter et al. |
| 9,740,921 B2 | 8/2017 | McClure et al. |
| 9,750,239 B2 | 9/2017 | Vilinskis et al. |
| 9,767,230 B2 | 9/2017 | Kimchi et al. |
| 9,799,207 B1 | 10/2017 | Tavares |
| 9,911,095 B2 | 3/2018 | Mashburn et al. |
| 9,986,313 B2 | 5/2018 | Schwarzkopf et al. |
| 10,026,300 B1 | 7/2018 | Hutz |
| 10,049,341 B2 | 8/2018 | Jones et al. |
| 10,079,903 B1 * | 9/2018 | Cunico ................. H04L 67/306 |
| 10,085,438 B1 | 10/2018 | Dismang |
| 10,111,416 B2 | 10/2018 | Rich et al. |
| 10,127,797 B2 | 11/2018 | Probin et al. |
| 10,152,035 B2 | 12/2018 | Reid et al. |
| 10,157,372 B2 | 12/2018 | Brailovskiy et al. |
| 10,192,194 B2 | 1/2019 | Bernhardt et al. |
| 10,325,241 B2 | 6/2019 | Haimi |
| 10,489,743 B2 | 11/2019 | Aepli |
| 2001/0033230 A1 | 10/2001 | Barber et al. |
| 2003/0058097 A1 * | 3/2003 | Saltzstein ................ G08B 1/08 340/531 |
| 2003/0213161 A1 | 11/2003 | Gardner et al. |
| 2004/0090329 A1 | 5/2004 | Hitt |
| 2004/0100394 A1 | 5/2004 | Hitt |
| 2005/0014482 A1 | 1/2005 | Holland et al. |
| 2005/0151653 A1 | 7/2005 | Chan et al. |
| 2005/0162279 A1 | 7/2005 | Marshall et al. |
| 2006/0240853 A1 | 10/2006 | Donner et al. |
| 2007/0030156 A1 | 2/2007 | Schlager et al. |
| 2007/0032830 A1 | 2/2007 | Bowers |
| 2008/0055094 A1 | 3/2008 | Barber et al. |
| 2008/0204253 A1 | 8/2008 | Cottee et al. |
| 2008/0210153 A1 | 9/2008 | Alvarado |
| 2009/0260276 A1 | 10/2009 | Kirsch et al. |
| 2010/0134301 A1 | 6/2010 | Borth et al. |
| 2010/0148956 A1 | 6/2010 | Song et al. |
| 2010/0176954 A1 | 7/2010 | Alvarado |
| 2010/0283610 A1 | 11/2010 | Wetzel et al. |
| 2011/0109460 A1 | 5/2011 | Lloyd et al. |
| 2011/0230160 A1 | 9/2011 | Felgate |
| 2011/0242043 A1 | 10/2011 | Yarvis et al. |
| 2011/0312286 A1 | 12/2011 | Lin et al. |
| 2012/0245969 A1 | 9/2012 | Campbell |
| 2013/0162443 A1 | 6/2013 | Oppenheimer et al. |
| 2013/0208575 A1 | 8/2013 | Sammut |
| 2014/0071276 A1 | 3/2014 | Seifer et al. |
| 2014/0085100 A1 | 3/2014 | Rich et al. |
| 2014/0087762 A1 | 3/2014 | Galvin et al. |
| 2014/0106677 A1 | 4/2014 | Altman |
| 2014/0118135 A1 * | 5/2014 | O'Brien ................. G08B 25/08 340/539.11 |
| 2014/0253377 A1 | 9/2014 | Scalisi et al. |
| 2015/0149235 A1 * | 5/2015 | Leung .................... G06Q 50/22 705/7.27 |
| 2015/0290392 A1 | 10/2015 | Henderson et al. |
| 2015/0351336 A1 | 12/2015 | Gilbert et al. |
| 2016/0018800 A1 * | 1/2016 | Gettings ................ G08C 17/02 700/19 |
| 2016/0048798 A1 | 2/2016 | Meyer et al. |
| 2016/0086475 A1 | 3/2016 | Rich et al. |
| 2016/0192865 A1 | 7/2016 | Datta et al. |
| 2016/0240074 A1 | 8/2016 | Probin et al. |
| 2016/0269533 A1 * | 9/2016 | Taylor .................. G08B 25/001 |
| 2016/0371952 A1 | 12/2016 | Felgate |
| 2016/0379176 A1 | 12/2016 | Brailovskiy et al. |
| 2017/0035042 A1 | 2/2017 | Ben-Dashan et al. |
| 2017/0111128 A1 | 4/2017 | Hammerschmidt et al. |
| 2017/0112116 A1 | 4/2017 | Ji et al. |
| 2017/0140632 A1 | 5/2017 | Klein et al. |
| 2017/0208426 A1 | 7/2017 | Komoni et al. |
| 2017/0215381 A1 | 8/2017 | Shen et al. |
| 2017/0231214 A1 | 8/2017 | Vaisblat et al. |
| 2017/0231215 A1 | 8/2017 | Barton |
| 2017/0246466 A1 * | 8/2017 | Murphy ............... A61N 1/3904 |
| 2017/0318796 A1 | 11/2017 | Vaisblat et al. |
| 2017/0360026 A1 | 12/2017 | Zirkle et al. |
| 2017/0374437 A1 | 12/2017 | Schwarzkopf et al. |
| 2018/0006719 A1 | 1/2018 | Cress et al. |
| 2018/0033289 A1 | 2/2018 | Lee |
| 2018/0075596 A1 | 3/2018 | Fryshman |
| 2018/0096581 A1 | 4/2018 | Daly, Jr. |
| 2018/0199172 A1 | 7/2018 | Boily et al. |
| 2018/0199565 A1 | 7/2018 | Zosimadis |
| 2018/0217228 A1 | 8/2018 | Edge et al. |
| 2018/0249696 A1 | 9/2018 | Daly, Jr. et al. |
| 2018/0254905 A1 | 9/2018 | Chun |
| 2018/0279603 A1 | 10/2018 | Madl et al. |
| 2018/0295831 A1 | 10/2018 | Reid et al. |
| 2018/0299842 A1 | 10/2018 | Reid et al. |

(56) References Cited

U.S. PATENT DOCUMENTS

| | | |
|---|---|---|
| 2018/0301918 A1 | 10/2018 | Lupo et al. |
| 2018/0322454 A1 | 11/2018 | Komoni |
| 2018/0338681 A1 | 11/2018 | Scherer et al. |
| 2018/0350227 A1 | 12/2018 | Komoni |
| 2019/0037829 A1 | 2/2019 | Laut et al. |
| 2019/0078930 A1 | 3/2019 | Ravulapati |
| 2019/0096058 A1 | 3/2019 | Fryshman |
| 2019/0111272 A1* | 4/2019 | Hochhalter .......... A61N 1/3904 |
| 2019/0121302 A1 | 4/2019 | Reid et al. |
| 2019/0141295 A1 | 5/2019 | Lazar |
| 2019/0200597 A1 | 7/2019 | Borth et al. |
| 2019/0230148 A1 | 7/2019 | Borlik |
| 2020/0005626 A1 | 1/2020 | Triventi et al. |
| 2020/0029550 A1 | 1/2020 | Koziar et al. |
| 2020/0045932 A1 | 2/2020 | Knight et al. |
| 2020/0134812 A1 | 4/2020 | Fryshman |

FOREIGN PATENT DOCUMENTS

| | | |
|---|---|---|
| CA | 2920216 A1 | 8/2016 |
| CN | 102413553 A | 4/2012 |
| CN | 102457932 A | 5/2012 |
| CN | 203799486 U | 8/2014 |
| CN | 105894760 A | 8/2016 |
| EP | 3059719 A1 | 8/2016 |
| EP | 3013141 B1 | 9/2019 |
| ES | 2691531 T3 | 11/2018 |
| RU | 179998 U1 | 5/2018 |
| WO | 0226033 A1 | 4/2002 |
| WO | 2002100170 A3 | 10/2003 |
| WO | 2007094974 A1 | 8/2007 |
| WO | 2008064033 A2 | 5/2008 |
| WO | 2010030346 A1 | 3/2010 |
| WO | 2017004701 A1 | 1/2017 |
| WO | 2017011916 A1 | 1/2017 |
| WO | 2017171281 A2 | 10/2017 |
| WO | 2018145880 A1 | 8/2018 |
| WO | 2019157536 A1 | 8/2019 |
| WO | 2019168855 A2 | 9/2019 |

OTHER PUBLICATIONS

Mekki et al., "A comparative study of LPWAN technologies for large-scale ICT deployment", ICT Express, Mar. 2019, pp. 1-7, vol. 5, Issue 1, Korean Institute of Communications and Information Sciences (KICS), production and hosting by Elsevier B.V., https://www.sciencedirect.com/science/article/pii/S2405959517302953?via%3Dihub.

Petric et al., "Measurements, Performance and Analysis of LoRa FABIAN, a real-world implementation of LPWAn", Personal, Indoor, and Mobile Radio Communications (PIMRC), 2016 IEEE 27th Annual International Symposium on Personal, Indoor, and Mobile Radio Communications, Sep 2016, Valencia, Spain. , https://hal-imt.archives-ouvertes.fr/hal-01331966.

Son et al., "A Design and Implementation of Forest-Fires Surveillance System based on Wireless Sensor Networks for South Korea Mountains", International Journal of Computer Science and Network Security, Sep. 2006, pp. 124-130, vol. 6 No. 9B, IJCSNS.org, Seoul, Korea.

Tim Urban, Everything You Should Know About Sound, Wait But Why, Mar. 9, 2019, https://waitbutwhy.com/2016/03/sound.html.

Yousef et al. "A low-cost LoRaWAN testbed for IoT: Implementation and measurements." Internet of Things (WF-IoT), 2018 IEEE 4th World Forum on. IEEE, 2018.

* cited by examiner

COMMAND SEQUENCE #1

As soon as connection is made to the database the GDS command is automatically sent from the unit.

If the GDS command is successfully received, then the connection shall be closed ONLY if ALL these conditions are met:
1. TRIGGER (unit_trigger) = 1 or 0
2. BATTERY (unit_battery) = 1 or 0
3. RESET (unit_reset) = 0
4. FORMAT (unit_format) = 0
5. unit_change database field = 0

If the GDS command is successfully received, then the connection must remain open if ANY of these conditions are met:

1. RESET (unit_reset) =1
2. FORMAT (unit_format) = 1
3. unit_change database field = 1
4. The UNIT SERIAL NUMBER received cannot be verified against a valid unit_serial in the database
5. IMEI cannot be verified for the record in the database (unit_imei)
6. ICCID cannot be verified in the database (unit_iccid)
7. That there is a DFOTA update GDS command:

Serial Number and Device Status is returned.

(T) TRIGGER (unit_trigger) – 0 = No Trigger, 1 = Trigger.
(B) BATTERY (unit_battery) – 0 = Battery good, 1 = Battery low
(R) RESET (unit_reset) – 0 = No reset, 1 = Unit has been reset
(F) FORMAT (unit_format) – 0 = No format, 1 = Unit has been formatted
(S) SERIAL NUMBER (unit_serial) -

If serial number is missing then new blank record is created with serial number.
If IMEI or ICCID are missing then those will be requested from the unit with the GDM and GDN command.
If TRIGGER (unit_trigger) = 1 then set off ALARM SEQUENCE in application ELSE do nothing
If BATTERY (unit_battery) = 1 then turn on low battery indicator ELSE do nothing If the RESET (unit_reset) OR FORMAT (unit_format) comes back with a "1" then go to COMMAND SEQUENCE #2 ELSE disconnect.

*FIG. 12A*

COMMAND SEQUENCE #2

Order of priority

If RESET (unit_reset) = 1 then send SDS command ELSE do nothing.
If FORMAT (unit_format) = 1 then send check firmware with GDF ELSE do nothing.
    Compare unit_currentfirmware with unit_newfirmware.
    If unit_currentfirmwware = unit_newfirmware then send SDS.
    If unit_currentfirmware is NOT EQUAL to unit_newfirmware then run firmware update sequence
If TRIGGER (unit_trigger) = 1 then set off ALARM SEQUENCE in application ELSE do nothing
If BATTERY (unit_battery) = 1 then turn on low battery indicator ELSE do nothing When complete the SDL command will be sent to the unit indicating it is done with the session.

*FIG. 12B*

SDS SEQUENCE

Before disconnecting from the unit if any of the following conditions are valid then the SDS command must be sent to the unit. Indicated by the CHANGE variable being set.

If RESET (unit_reset) or FORMAT (unit_format) was set ("1").
If SENSITIVITY (unit_sensitivity) has been changed by the user.
If SPEAKER (unit_sound) has been changed by the user.
If DEACTIVATE (isActiavted) has been changed by the user When complete the SDL command will be sent to the unit indicating it is done with the session.

*FIG. 12C*

ALARM SEQUENCE

If PAUSE (unit_pause) > 0 then send SDP command then RETURN ELSE continue.
Look up notification recipients from subscriber DB record associated with device ID.
For each notification recipient handle associated with device ID:
    Format notification message appropriate for corresponding delivery service
    Send formatted notification message to handle using corresponding delivery service
In the application the alarm indictor and/or sound effect should be triggered. The alarm indictor should have a place to push to acknowledge with an available PAUSE button. The pause should be selectable in 1-minutes increments up to 4320 (72 Hours). Once the number of pause is selected by the user and the confirm button is pressed then this information shall be stored in a database field called unit_pause.

*FIG. 12D*

PAUSE SEQUENCE – Active when PAUSE > 0

The PAUSE variable (unit_pause) would be decremented each minute IF it is > 0.

*FIG. 12E*

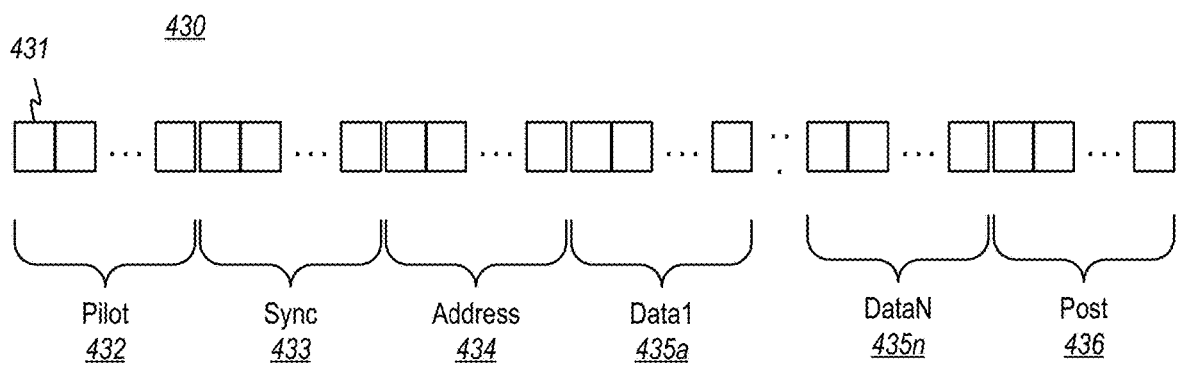

*FIG. 15*

AUTOMATED EXTERNAL DEFIBRILLATOR (AED) MONITORING SERVICE

CROSS-REFERENCE TO RELATED APPLICATIONS

This application is a continuation of U.S. patent application Ser. No. 16/183,732, filed Nov. 8, 2018, which claims the benefit of U.S. Provisional Patent Application No. 62/682,508, filed Nov. 7, 2017 and of U.S. Provisional Patent Application No. 62/752,284, filed Oct. 29, 2018, each of which is incorporated by reference herein in its entirety.

BACKGROUND

Aspects of the invention relate generally to the monitoring and location tracking of an Automated External Defibrillator (AED).

An automated external defibrillator (AED) is a portable electronic device that automatically diagnoses the life-threatening cardiac arrhythmias of ventricular fibrillation and pulseless ventricular tachycardia and can treat them through defibrillation. Defibrillation is the application of electrical therapy which stops the arrhythmia, allowing the heart to reestablish an effective rhythm. For every minute that a person in cardiac arrest goes without being successfully treated by defibrillation, the chance of survival decreases by 7 percent per minute in the first 3 minutes and decreases by 10 percent per minute as time advances beyond 3 minutes.

In public places, and in workplaces and industrial areas, AEDs are typically installed in a semi-permanent location, often in a cabinet and/or behind glass that is well marked with potentially bright colors to alert people in the vicinity of the presence of the AED in case of emergency. AEDs often stay in the cabinet or initial location for long periods of time.

However, occasionally they are subject to unauthorized tampering by people in a non-emergency situation. Occasionally, after use in an emergency situation, they are not returned to their original location. When the AED is not in its designated location, it can cause problems the next time use of the AED is needed. Emergency personnel may not be able to locate the AED when they need it. In other situations, emergency personnel arrive on a scene and need an AED but simply do not know where it is located in a building. It would therefore be desirable to have a solution for locating the nearest AED and for monitoring in real-time when an AED has been moved and for being able to identify its potential new location.

SUMMARY

One or more aspects of the invention include an AED monitoring service which both monitors in real-time when an AED has been moved and identifies its potential new location. This location and movement information can be displayed on a desktop or mobile application where all AED's in the vicinity of patient and potential first responders are available for access.

The needs in the art are satisfied by the present invention which is a "smart tracker" that is attached to the AED device as a separate standalone device. The attachment method of the smart tracker device to the AED is one of many possible methods including but not limited to having the smart tracker embedded internally in the AED and its electronics package. This smart tracker has built in long lasting battery powered electronics that allow it to detect when the AED has been moved and reports this information via the cellular network or Low-Power Wide Area Network (LPWAN) network. The use of the cellular network and LPWAN allows for an extremely reliable connection and does not require any other end-user configuration compared to that of a localized WiFi network where setups require a more detailed interaction and have a higher rate of connectivity failure.

When an AED device is moved an internal sensor on the smart tracker reports this information in real-time through the cellular or LPWAN connection to a service executing on a computer which is connected to a centralized database. In a preferred embodiment, the computer and centralized database are located in the "cloud". The cloud-based service identifies the specific AED based on the information received from the specific AED and reports the movement via email, text or an application to alert the owner or monitor of the device. The owner or monitor may use this information to alert the police or emergency personnel of the movement of the AED for a potential emergency event or possible theft of the device. These are a few examples of many possible types of alerts, it will be understood that variations of alerts and the methods to contact the owner or monitor can be used within the spirit and scope of the invention as described herein.

Additionally, in an embodiment, when an AED device is installed the smart tracker may report back its GPS location via the cellular or other LPWAN connection to a to a centralized database to a computer in the "cloud". The cloud-based computer would keep track of these locations which would be made available to a specially designed software application. This application would display these AED locations using a map overlay using the acquired GPS information. The application could be used by emergency personnel or other first responders that arrived at the scene without an AED, if the AED owner chooses to make public the location of the device through the software application.

In an embodiment, an automated external defibrillator (AED) monitoring service is connected by a network to receive communications from a remote AED monitoring device that senses conditions at a remote AED system. The remote AED monitoring device generates an alert message upon its detection of a sensed condition event at the AED monitoring device. The alert message includes information related to identification of the monitored remote AED system and the sensed event. The AED monitoring service executes on a computer accessible via a network. The computer comprises at least one computer processor and computer readable storage memory that stores program instructions which, when executed by the at least one computer processor, implements performance by the computer of the AED monitoring service. When executed, the program instructions implement a step of receiving the alert message from a remote automated external defibrillator (AED) monitoring device. The receipt of the alert message by the AED monitoring service initiates a sequence of communications between the remote AED monitoring device and the monitoring service. The program instructions further implement extracting and processing the identification information to extract an identifier associated with the remote AED monitoring device and extracting and processing the sensed event information to determine an event associated with the sensed event information. The program instructions implement generating a notification message indicating occurrence of the determined event at the monitored remote AED associated with the extracted remote AED monitoring device identifier, retrieving from an electronic database an electronic delivery address associated with the extracted remote AED monitoring device identifier and a corresponding electronic delivery service identifier associated with the retrieved electronic delivery address, and sending the alert notification message to the retrieved electronic delivery address using an electronic delivery service identified by the retrieved electronic delivery service identifier. The program instructions further implement retrieving from the electronic database control information associated with the remote AED monitoring device identifier, and based on the retrieved control information, determining whether any intercommunication actions with the remote AED monitoring device are required, performing said determined required intercommunication actions, if any, with the remote AED monitoring device, and signaling the remote AED monitoring device to place itself into a low-power mode. The AED monitoring service can communicate with the remote AED monitoring device only upon initiation of communications by the remote AED monitoring device.

BRIEF DESCRIPTION OF THE DRAWING

The disclosure and the following detailed description of certain embodiments thereof may be understood by reference to the following figures:

FIGS. 12A-12E are operational flow of command sequences performed by the Notification Service in conjunction with the MDAD;

FIG. 15 is a high-level format of a message that is transmitted by a sensor.

DETAILED DESCRIPTION

Figure 1:
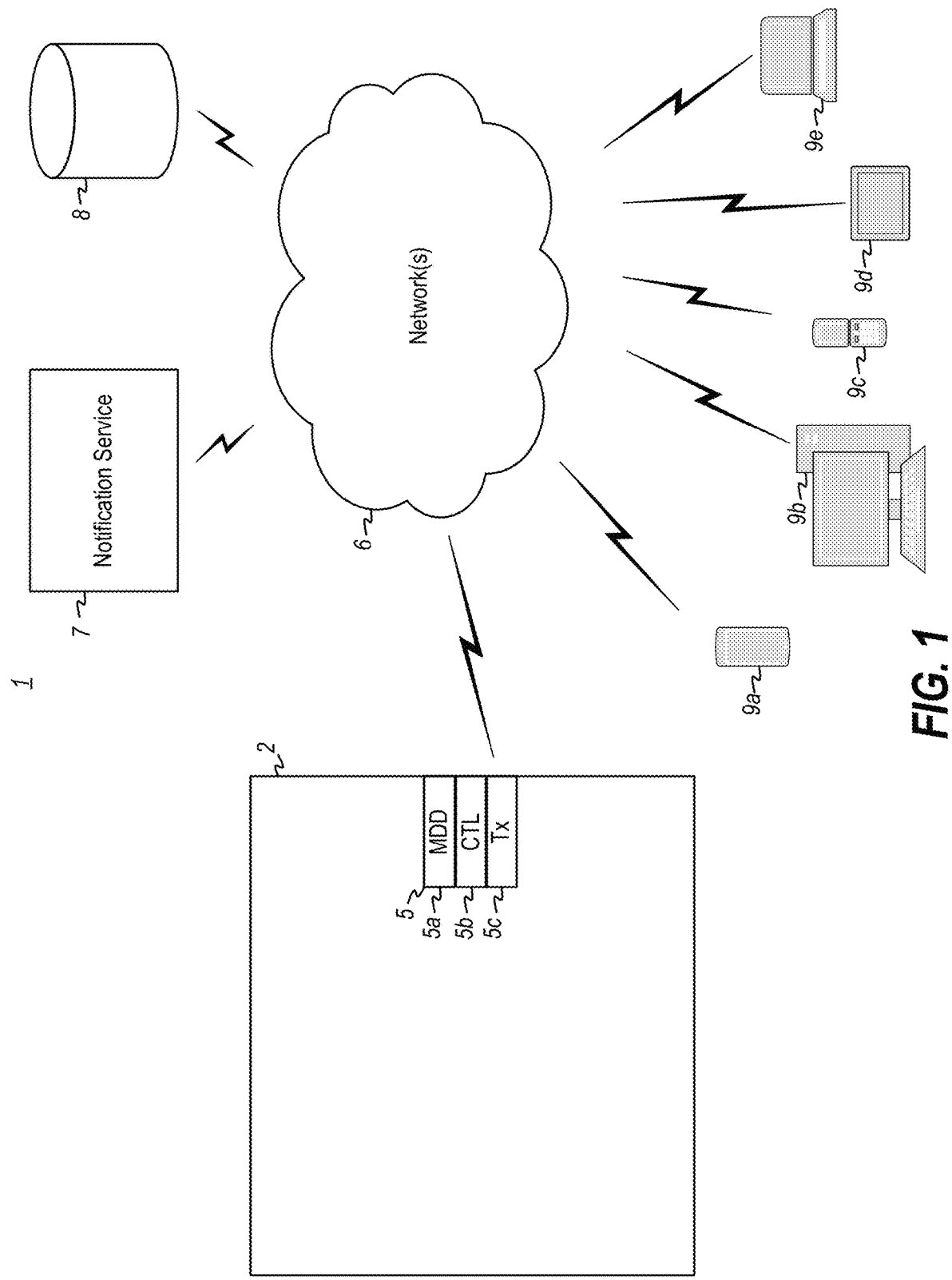
FIG. 1 is a system diagram of an exemplary environment implementing an AED monitoring system 1 in accordance with an embodiment of the invention

FIG. 1 is a system diagram of an exemplary environment implementing an AED monitoring system 1 in accordance with an embodiment of the invention. In general, an AED monitoring system 1 includes an Automated External Defibrillator (AED) 2 having attached thereto or embedded or integrated therein a movement detection and alerting device (MDAD) 5. The MDAD 5 includes a movement detection device (MDD) 5*a*, a controller (CTL) 5*b*, and a radio transmission module (RTM) 5*c*. The movement detection device 5*a* detects movement of the AED 2. The controller 5*b* is responsive to movement detection by the movement detection device 5*a* and generates notification messages for transmission by the radio transmission module 5*c*, via one or more networks 6, to a remote monitoring service 7 (also referred to herein as notification service 7 or Notification Service 7). The MDAD 5 is registered with the notification service 7. In a preferred embodiment the notification service 7 is accessible via a packet data network such as the Internet, but it is to be understood that the notification message may be transmitted from the MDAD 5 and routed to the notification service 7 across multiple different networks having different physical and logical communication stacks/protocols, such as one or more different cellular networks and/or one or more different packet data networks.

Because the MDAD 5 may be separate from the AED 2, or may be attached to, embedded in, integrated into or otherwise associated with the AED 2, the use of the term "AED/MDAD" herein refers to the combined unit of the AED and MDAD, regardless of the form of the combination, so long as the MDAD is able to detect movement of the AED. In an embodiment, the MDAD 5 is a separate unit that is attached to existing AED units via Velcro, glue, epoxy, screws, hook(s), carabiner(s), ring(s), etc. In an alternative embodiment the MDAD 5 is embedded and/or integrated into the electronics of the AED 2, or is integrated as a separate device inside the enclosure of the AED 2.

The notification service 7 stores registration information in a database 8. The registration information stored in the database 8 includes the device identifier for each AED 2/MDAD 5 that is registered with the notification service 7, along with corresponding recipient and delivery service information associated therewith. In an embodiment, the database 8 stores the device ID of each registered device (AED 2 or MDAD 5), along with, for each device ID, one or more delivery addresses and corresponding indications of electronic delivery services which are to be used to deliver a notification to the corresponding respective delivery addresses. Such a schema allows for notification to one or more notification recipients via various notification delivery mechanisms. For example, for a given registered device (AED 2 or MDAD 5), notification may be sent to one or more recipients via their respective chosen notification methodology (e.g., email, SMS text, in-app push notification, etc.) so that they can receive notification via their respective preferred technology.

For example, for a given registered device (AED 2 or MDAD 5), the device may be configured such that a notification is delivered via email to a particular user's (a "recipient") email address, via SMS text to a recipient's mobile phone number, and to a recipient's app executing on the recipient's smart phone (and addressed via the smart phone number or email address). A different registered device (AED 2 or MDAD 5) (not shown) having a different device ID may be configured such that a notification is delivered, for example, only via SMS text to a different recipient's mobile phone number. The described registration schema contemplates the ability to allow different registered devices (AED 2 or MDAD 5) to be individually configured such that notification recipient information and preferences can be specified on a device-by-device basis. In embodiments, users of the notification service 7 can select the delivery service(s) and corresponding notification recipients to be notified by the service, via a web-enabled app, a website portal or API. While it is contemplated that the notification service 7 supports user-configurable notification preferences, it is also within the scope of the invention that the delivery service(s) and recipients are predetermined by an administrator, and enterprise-level entity or other entity.

In operation, upon detection of movement of the AED 2 (and potentially upon the detection of one or more additional environmental and/or the calculation of one or more conditions based on a calculated or state machine condition or state in the MDAD 5), the MDAD 5 sends an alert, via the radio transmission module 5c and over one or more networks 6, to the notification service 7. Upon receiving an alert from a MDAD 5, the notification service 7 determines the device ID of the AED 2/MDAD 5 that sourced the alert, identifies the delivery addresses and corresponding electronic delivery services by which notification recipients associated with the device ID are to be notified, and sends a notification to, preferably each of, the identified delivery addresses associated with the device ID via the identified corresponding delivery services. In this way, notification recipients of electronic messages accessed on remote devices 9 (such as but not limited to one or more smartphones 9a, computers 9b, cell phones 9c, tablets 9d, and/or laptops 9e, collectively 9) can be informed when the AED 2 is moved from its original location.

Figure 2:
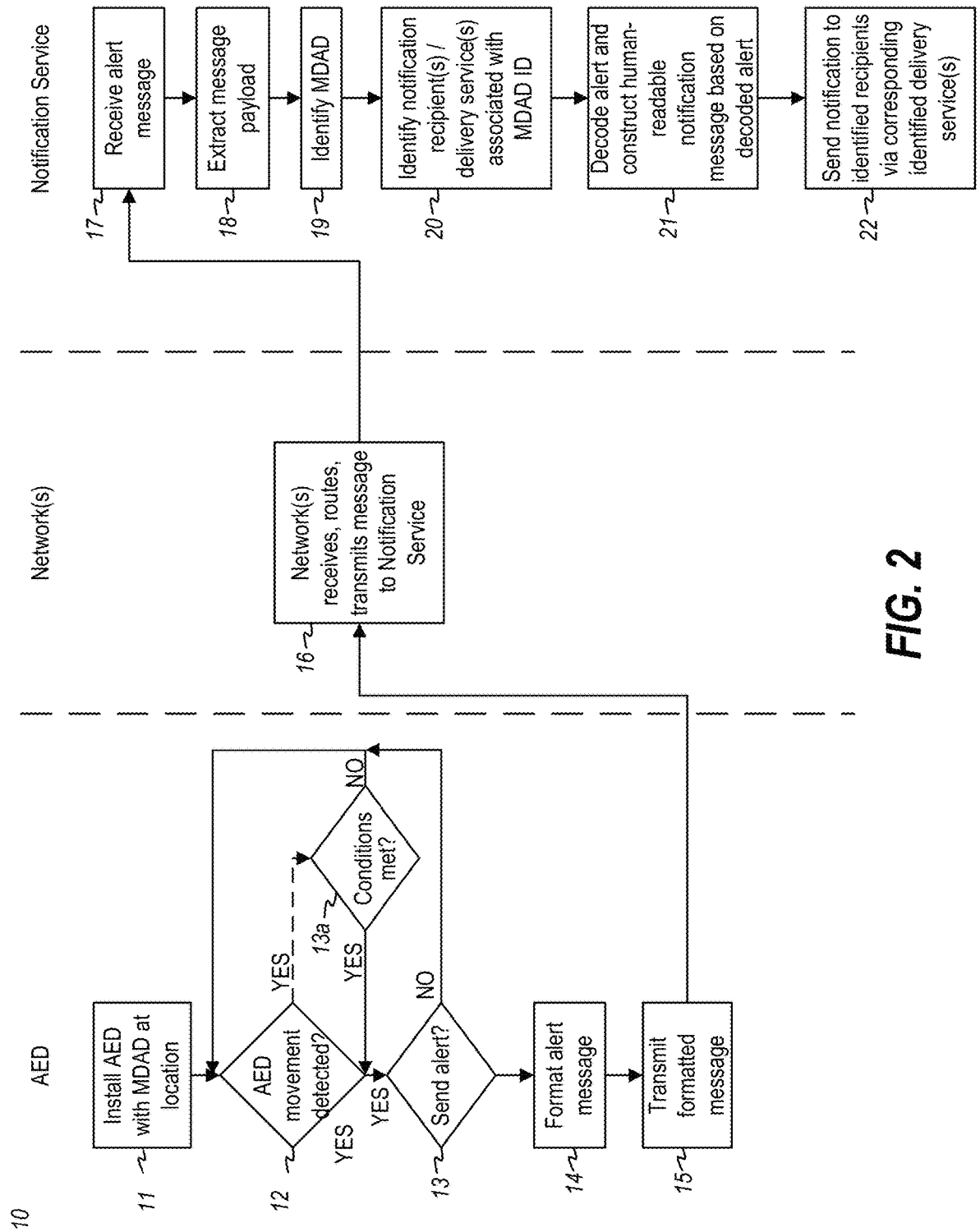
FIG. 2 is a flowchart illustrating an exemplary embodiment of a notification service method 10 for notifying recipients of a detected movement of an AED.

FIG. 2 is a flowchart illustrating an exemplary embodiment of a notification service method 10 for notifying recipients of a detected movement of an AED. According to the method 10, an AED 2 having an MDAD 5 attached to, embedded in, integrated with or otherwise associated with, is installed at a location (step 11). When the AED is moved from its location, the MDAD 5 detects the movement (step 12), optionally performs pre-processing to determine whether to send an alert to the notification service 7 (step 13a), and upon determination to send an alert (step 13), formats an alert message (step 14) and transmits the alert message to the notification service 7 (step 15). In an embodiment, the MDAD controller 5b formats an alert message that contains at least a device identifier (the device ID) of the AED 2 and/or MDAD 5, and an alert code or other message that may be processed by the notification service 7 for use in notifying notification recipients associated with the AED 2/MDAD 5. In an embodiment, the controller 5b coordinates with the transmission module 5c to send the alert message to the notification service 7. The transmission module 5c transmits the alert message (using the appropriate network protocol) where it is received by a remote receiver in a radio access network (included in network(s) 6), and may be further transmitted, routed, processed (step 16), and ultimately received (step 17) via the network(s) 6, processed and decoded by the notification service 7.

The notification service 7 receives the alert message, processes the message to extract the message payload (i.e., the substantive contents of the message) (step 18), and decodes the alert message to identify the AED 2/MDAD 5 which sent the alert (step 19). The payload of the message contains the AED/MDAD ID. The notification service 7 uses the AED/MDAD ID to look up or otherwise identify one or a list of notification recipients who should receive a notification message and the corresponding delivery service(s) by which each recipient should be notified (e.g., text, email, voicemail, in-app notification, etc.) (step 20).

The extracted payload of the message also includes a code indicating the substantive alert condition, namely that the AED 2 has been moved, from the sending MDAD 5. In a preferred embodiment, as discussed hereinafter, the extracted payload also includes location information, such as current GPS coordinates of the AED 2. The notification service 7 decodes the code (and location information if available) and constructs a human readable message in the appropriate format of the delivery service(s) for each identified delivery service corresponding to each notification recipient (step 21). Delivery services may include such services such as a text (SMS) delivery service, an email delivery service, an in-app notification delivery service, a voicemail delivery service, or other type of delivery service that delivers content such as text, audio, video, images, app-push notifications, etc., to an end-user device. The format of the human-understandable message will depend on the particular delivery service. For example, an SMS delivery service requires a text message; an email message requires text or an attachment, a voicemail delivery service requires an audio file containing human-understandable audio content, an in-app notification delivery service may contain text, an image containing human-understandable message, an audio/video clip, a document, etc. If location information is available, preferably the message includes the location of the AED 2 as reported from the AED 2/MDAD 5 via the alert message.

The notification service 7 then sends the constructed notification message(s) via the corresponding delivery service(s) to the notification recipient delivery address(es) for the identified notification recipient(s) associated with the identified MDAD 5 (step 22).

Figure 3:
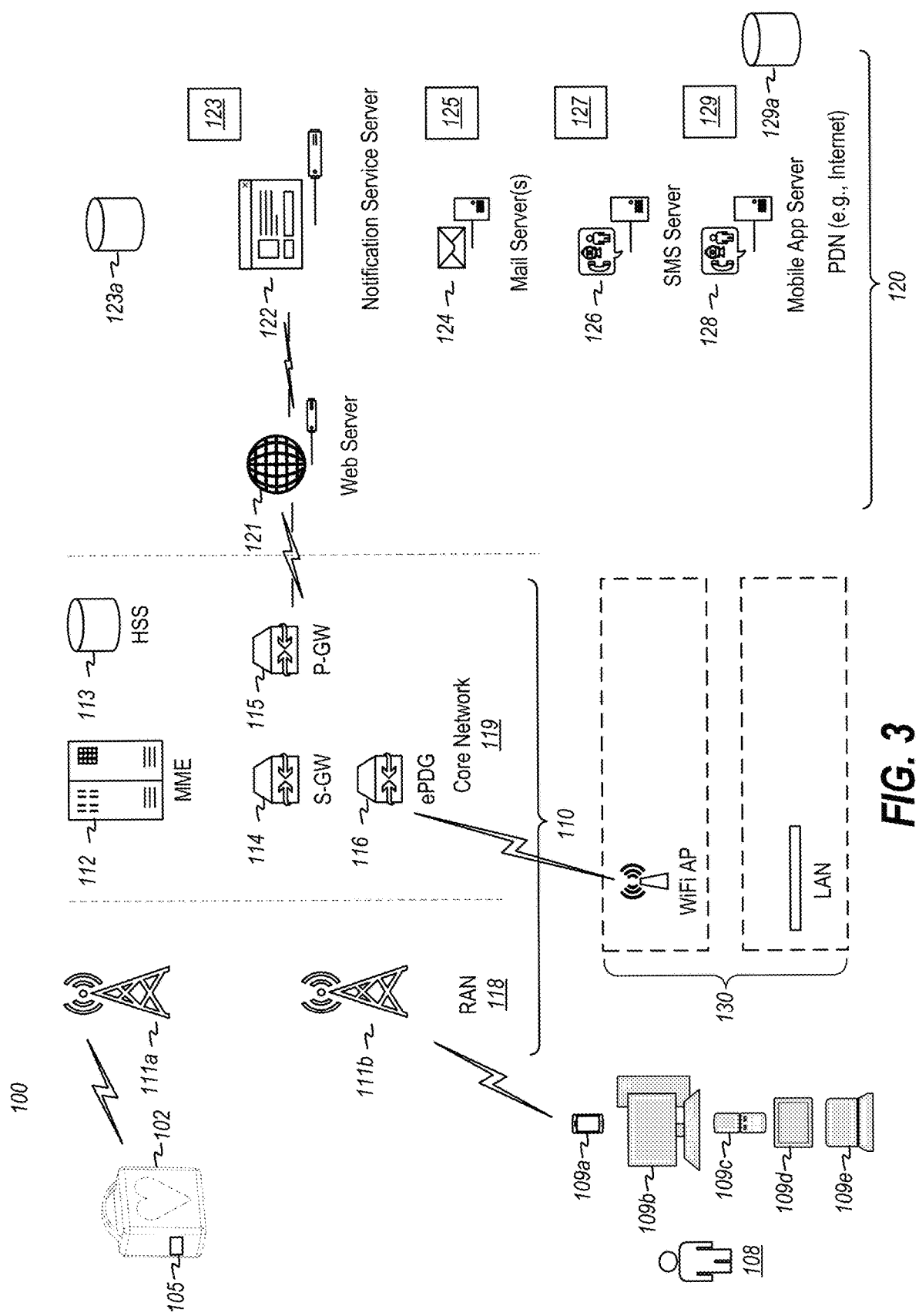
FIG. 3 is a network architecture diagram of an embodiment of an environment 100 implementing a smart AED movement tracking system.

FIG. 3 is a network architecture diagram of an embodiment of an environment 100 implementing a smart AED movement tracking system. Although not limited to the environment shown which uses a cellular network as the gateway connection to a packet-switched network such as the "cloud" and/or Internet, in a preferred embodiment, the system is designed such that an AED 2/MDAD 105 can be installed in remote locations that may not have access to power and/or may not have (reliable) WiFi for accessing the Internet 120, yet can still transmit alert messages to a Notification Service 123 which is connected to the Internet 120. With these parameters in mind, power to the MDAD 105 is therefore preferably supplied solely from a battery supply (or optionally a standalone power source such as a solar power supply), and the MDAD 105 accesses the Internet 120 to communicate with the Notification Service 123 using a Low-Power Wide Area Network (LPWAN) such as a Low-power cellular network (for example, a CAT-M1, CAT-NB1 or EGSM-IoT enabled network). In the environment 100 shown in FIG. 3, an AED 102 having an MDAD 105 attached, embedded, integrated, or otherwise associated therewith is placed in a location. The MDAD 105 of the AED 102 monitors the AED 2 for movement. Movement may include vibrational movement which can occur when a person or object interacts with the AED 102, and may also include geo-locational movement which can occur when someone moves the AED 102 from one location to another. Upon detection of movement, the MDAD 105 may connect, via a Low-Power Cellular Network 110 (shown as an LTE-M (or Long Term Evolution enhanced Machine Type Communication) network) to the Internet, to send an alert message to the Notification Service 123 (which is connected to the Internet 123 by way of a Notification Service server 122 connected to the Internet 120).

Figure 4:
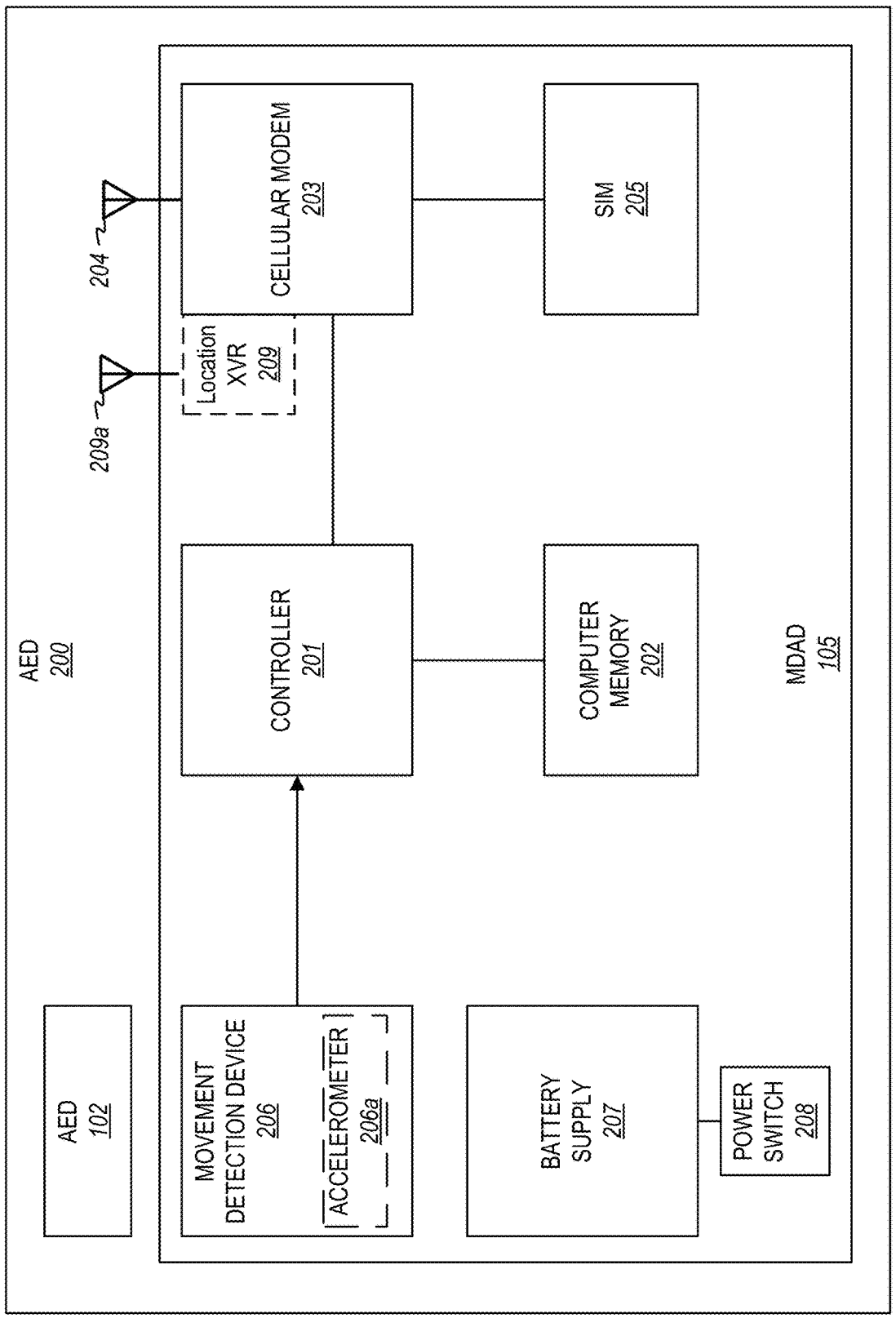
FIG. 4 is a schematic block diagram of an embodiment of a trackable AED.

Turning in more detail to an exemplary embodiment of an AED, FIG. 4 is a schematic block diagram of an embodiment of a trackable AED 200 comprising an AED 102 and having a movement detection and alerting device (MDAD) 105 attached to, embedded in, integrated with, connected to, or otherwise associated therewith that may be used to implement the AED 102 with MDAD 105 of FIG. 3 (and/or AED 2/MDAD 5 FIG. 1). As shown in FIG. 4, the trackable AED 200 comprises an AED 102 and an MDAD 105. The MDAD 105 includes a controller 201, computer memory 202 which stores program instructions and data (including a unique serial number (SN) of the AED 102 and/or MDAD 105), a cellular modem 203 which includes internal memory and stores an International Mobile Equipment Identifier (IMEI), an antenna 204, a Subscriber Identity Module (SIM) 205 that stores a unique Integrated Circuit Card Identifier (ICCID), a movement detection device 206, and a battery supply 207 which is electrically coupled to, and supplies power to, all the electronic components of the MDAD 105.

The controller 201 may be a microprocessor, a computer processing unit (CPU), a microcontroller unit (MCU), or custom application specific integrated circuit (ASIC), or other integrated circuit (IC), or non-integrated circuitry, that is electrically coupled to (directly or indirectly), or has embedded therein, computer memory 202. Computer memory 202 comprises computer readable storage media, preferably in the form of one or more, or any combination, of Programmable Read-Only Memory (PROM, EPROM, EEPROM, flash EPROM), and/or Random Access Memory (RAM, DRAM, SRAM, SDRAM, etc.). Computer memory 202 stores program instructions executable by the controller 201 to perform one or more operative steps for implementing various aspects of the invention. The computer memory 202 further stores data which may be used by the controller 201 in its operations. The computer memory 202 may be integrated or embedded within the integrated circuit (IC) implementing the controller 201 or may be standalone memory IC(s) electrically coupled to the controller via one or more busses.

The cellular modem 203 is electronic circuitry typically fabricated in the form of an integrated circuit (IC) that contains the hardware and control functions for implementing the RF communication. In particular, a typical cellular modem 203 contains a controller/CPU, integrated computer memory, signal encoding/decoding circuitry, a power amplifier, and a baseband processor which includes multiplexing/demultiplexing, channel selection, carrier generation, and modulation circuitry. In an embodiment, the cellular modem 203 is responsive to telephone Attention (AT) commands for controlling the modem and converts digital messages into RF transmission signal suitable for the network on which it is transmitted. For example, where the cellular modem 203 is implemented to connect to an LTE-M cellular network, the cellular modem 203 is configured to transmit signals on the antenna 204 according to a CAT-M1 protocol. The cellular modem 203 is further configured to receive RF signals carrying messages from the Notification Service 123 (FIG. 3) and to convert the received signals into a digital format recognizable by the controller 201.

The movement detection device 206 comprises one or more sensors that detects movement and/or vibration and generates at least one output signal based on detected movement/vibration. In an embodiment, the movement detection device generates, on at least one output port (such as one or more wires, pins or pads), an output signal representative of a movement. In an embodiment, the movement detection device 206 is an electronic accelerometer 206a, which measures acceleration and direction of acceleration in response to movement or vibration. Alternatively, the movement detection device 206 could comprise a GPS module (not shown) which receives positioning signals from a Global Positioning System and compares present location to recent past location to detect whether the AED. Where the movement detection device 206 includes a GPS module, the computer memory 202 may store initial and/or present location information, and further may store one or more additional location information acquired by the GPS module over a period of time. In an embodiment, the output signal may be a signal between two voltage rail values (e.g., for purposes of example only and not limitation a low rail value of 0V and a high rail value of 1.8-3.3 V) and the voltage level of the output signal is representative of the magnitude of acceleration/vibration. Additional signals may include the direction of acceleration. In an alternative embodiment, the output signal of the movement detection device 206 is a binary signal which is mapped in a first state (either low or high voltage) when no movement/acceleration is detected or when detected movement/acceleration is (at or) below a trigger threshold, and in a second state (voltage level being the opposite of the first state) when detected movement/acceleration is (at or) above the trigger (or a second trigger) threshold.

Structurally, the controller 201 is electrically coupled to the movement detection device 206 and the cellular modem 203. The movement detection device 206, which is arranged to detect movement and/or acceleration, is also arranged to detect sounds and so herein is also referred to herein as a sound detection sensor 206. In an embodiment, the controller 201 is a microprocessor or microcontroller capable of receiving interrupt signals and processing interrupt service routines. In such embodiment, the controller 201 is coupled, directly or indirectly, to receive the output signal(s) of the movement detection device 206 and executes hardware logic or program instructions based on the received output signal (s). Generally, when the movement detection device 206 detects movement/acceleration at or above a predetermined threshold level, it generates one or more output signal(s) indicating the condition. In an embodiment, the controller 201 comprises a microprocessor that can process an interrupt received on an interrupt input port (e.g., a pin or pad of the microprocessor). The movement detection device 206 generates a trigger signal on an output port of the movement detection device 206. The output port of the movement detection device 206 is electrically coupled (directly or indirectly) to the interrupt input port of the controller 201, and the signal present on the output port of the movement detection device 206 serves as an interrupt signal to the controller. When the output signal of the movement detection device 206 indicates that it is in a triggered state (indicating movement/acceleration detected (at or) above a trigger threshold), it generates an interrupt within the controller 201, causing the controller 201 to run an interrupt service routine to perform several actions. In particular, the controller 201 may formulate an alert message and send commands to the cellular modem 203 to transmit the alert message.

The cellular modem 203 adheres to a predetermined transmission protocol stack, as predefined based on the protocol used for communicating with the cellular service to which the MDAD 105/200 subscribes. As is required generally for cellular modems that need to pass messages from a mobile device through a cellular network to a packet data network (e.g., the Internet), the cellular modem 203 includes circuitry and programming to encode an alert message generated by the controller 201, encapsulate the encoded message into one or more packets, and perform the signal processing required to adhere to the data transmission scheme(s) recognized and used by the cellular network 110 for data uplink (from MDAD 105 to cellular network 110) and data downlink (from cellular network 110 to MDAD 105). For example, in an LTE-M enabled cellular network, the cellular modem 203 is preferably capable of packetizing data in accordance with TCP/IP or UDP protocol, and includes hardware that transmits packet data according to a SC-FDMA, 15 KHz tone spacing, Turbo Code, 16 QAM modulation scheme, and receives data based on OFDMA, 15 KHz tone spacing, Turbo Code, 16 QAM modulation scheme. Other types of cellular networks use different modulation schemes implemented in accordance with the standards promulgated by worldwide organizations such as $3^{rd}$ Generation Partnership Project (3GPP), Institute of Electrical and Electronics Engineers (IEEE), and Global System for Mobile Communications Association (GSMA), and may alternatively be used as the gateway connection to a packet-switched data network (such as the Internet) for subsequent transmission of alert messages to the Notification Service 123.

As described previously, due to the design parameters for the MDAD 105 having a stand-alone power supply 207, the MDAD 105 is preferably implemented using ultra-low-power components. By way of example and not limitation, in an embodiment, the controller 201 comprises an ultra-low-power microcontroller unit (MCU) with integrated flash memory and an integrated EEPROM such as an STMicroelectronics STM8L151C8 IC, which consumes 200 uA in normal operating mode and less than 6 uA when placed in a low-power mode.

Further, in an embodiment and by way of example and not limitation, the cellular modem 203 is implemented using a Quectel LPWA Module BG96, manufactured by Quectel Wireless Solutions Co., Ltd., headquartered in Shanghai, China. The Quectel BG96 Cat-M1/NB1 & EGPRS Module can transmit according to CAT-M1 or CAT-NB1 protocols over existing LTE/Extended GPRS (EGPRS) networks, consuming only 10 uA in a low-power mode (Power Saving Mode (PSM) and 190 mA when transmitting at 23 dBm. The Quectel BG96 is programmed to use CAT-M1 protocol when connecting to an LTE-M cellular network and is programmed to use CAT-NB1 protocol when connecting to an NB-IoT enabled cellular network.

Further in an embodiment and by way of example and not limitation, the movement detection device 206 is preferably an ultra-low-power device such as Micro-Electro-Mechanical Systems (MEMS) accelerometer or MEMS microphone that is implemented using microfabricated miniaturized electro-mechanical elements (on the order of micro, femto and nano-meters) and which by design consume very low power. In an embodiment, the movement detection device 206 is implemented using a STMicroelectronics LIS2DE12, which is a 3-axis MEMS accelerometer characterized by ultra-low-power consumption down to 2 uA and allows for programmable sensitivity. An accelerometer may be used as a movement detection device 206 by measuring the acceleration of multiple moving micro-parts, such as a diaphragm or other anchored movable micro-objects. The LIS2DE12 MEMS accelerometer is fabricated using micromachined silicon structures that are anchored at a few points and are free to move in the direction of acceleration. Sensing element(s) within the LIS2DE12 sense displacement of the silicon structures from their nominal positions resulting in a change in capacitance thereof and can be measured using charge integration in response to a voltage pulse applied to the capacitor structure. When an acceleration is applied to the sensor, the mass of silicon structures displaces from their nominal positions, which can be measured using a capacitive half-bridge. The change in capacitance is measured using charge integration in response to a voltage pulse applied to the capacitor. At steady state, the nominal value of the capacitors is a few pF and when an acceleration is applied, the maximum variation of the capacitive load is in the fF range. The LIS2DE12 MEMs accelerometer can be programmed to generate an interrupt upon detection of different levels of acceleration (measured in g's). The LIS2DE12 provides full scales of ±2 g/±4 g/±8 g/±16 g and is capable of measuring accelerations with output data rates from 1 Hz to 5.3 kHz.

The movement detection device 206 may alternatively be implemented using a GPS module, described hereinafter.

Further to the requirements of a limited battery power supply, the MDAD 200 preferably implements several power conservation techniques, including employing a controller 201 and a cellular modem 203 that can each be placed in a low-power mode (alternatively referred to as a Power Saving Mode (PSM)) state, whereby features of the controller 201 and cellular modem 203 which draw higher power are shut down and/or placed in a sleep mode when the respective devices are placed in the PSM state. For example, the cellular modem 203 turns off power to the antenna 204 when in the PSM state. The selection of the cellular modem 203 must of course consider the network over which alert messages are to be transmitted to ensure that the cellular modem 203 can transmit according to the protocol required by the selected network. To conserve battery power, in a preferred embodiment the MDAD 200 is implemented to communicate using a low-power signal over a LPWAN such as an LTE-CATM1, NB-IoT, or EC-GSM-1° T network, which specifies a transmission signal strength of 23 dBm.

Figure 5:
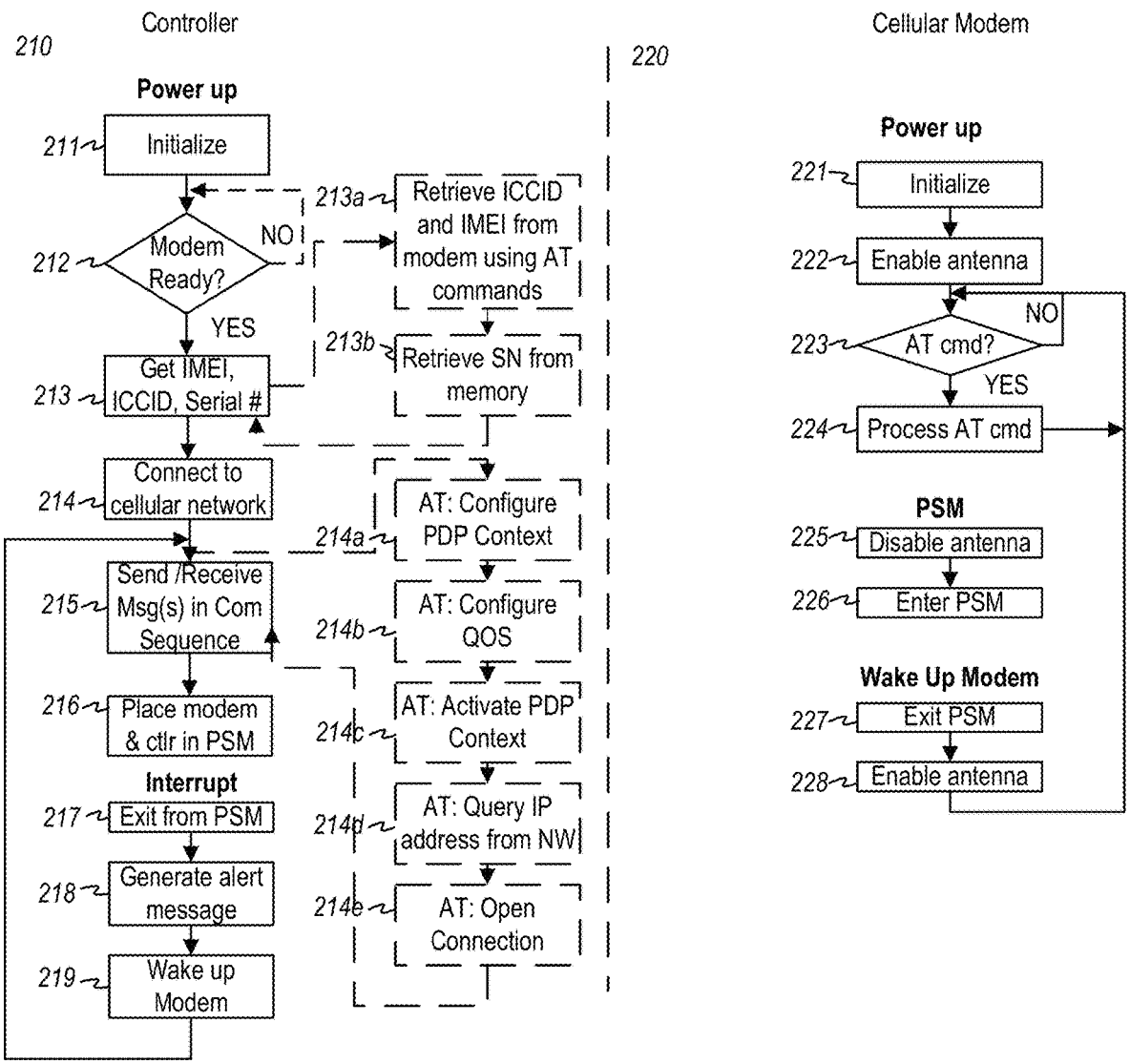
FIG. 5 is a flowchart illustrating an exemplary operation of a movement detection and alerting device (MDAD)

FIG. 5 is a flowchart illustrating an exemplary operation 210 of the MDAD 105. As shown, in operation, when the MDAD 105 is powered on, for example by turning on a power switch 208, the controller 201 and cellular modem 203 both perform an initialization. Once the controller 201 is initialized to a ready state (step 211), it monitors the Ready status (typically the output state of a pin on the cellular modem IC) of the cellular modem 203 (step 212). At first power up of the cellular modem 203, the cellular modem 203 performs an initialization (step 221), including readying the antenna 204 for transmission and/or reception (step 222). Once the cellular modem 203 has completed initialization and the antenna 204 is ready to transmit and/or receive, the controller 203 obtains the ICCID, and the IMEI and serial number of the device (step 213). In an embodiment, the ICCID is integrated into the SIM 205, and the controller 203 instructs the cellular modem 203 to access the SIM 205 to obtain the ICCID of the SIM 205. In an embodiment, the IMEI is programmed into an Electrically-Erasable Programmable Read-Only Memory (EEPROM) embedded in the cellular modem 203, and the controller 203 issues a command to the cellular modem 203 to obtain it. In an embodiment, the manufacturer of the MDAD 200 issues a unique serial number for each MDAD at the time of manufacture and stores it in a Programmable Read-Only Memory (PROM) or other memory 202 accessible by the controller 201.

Once the ICCID, IMEI and Serial Number of the device are obtained, the controller 201 then instructs the cellular modem 203 to connect to the subscriber network 110 (FIG. 3) (step 214). The cellular modem 203 is programmed to recognize various AT commands, which are commands to control communication using the modem. In an embodiment, the cellular modem 203 is configured with an embedded TCP/IP protocol stack, and the AT commands are translated into messages/responses, encapsulated into TCP/IP packets and transported over the cellular network 110 according to the TCP/IP protocol. In an embodiment, the controller 201 instructs the cellular modem 203 to connect to the subscriber network 110 by (1) configuring a Packet Data Protocol (PDP) Context with the network Access Point Name (APN), the subscriber name, password and authorization type (step 214a), (2) configuring the Quality of Service (QoS) settings (step 214b), (3) activating the PDP Context (step 214c), (4) querying the network for the IP address of the PDP context (step 214d), and (5) opening the connection (step 214e). Once the connection is open, the MDAD 5 can send and/or receive requests, commands, responses, and data (step 215) to/from the Notification Service 123. In an embodiment, the send/receive step 215 may include sending device status, movement detection alerts, location information, and communication acknowledgements to the Notification Service 123, and receiving communication acknowledgements, messages, or settings or firmware updates from the Notification Service 123.

In order to conserve power, the controller 201 is programmed to execute sequences of communication handshakes that comprise a series of requests (which may contain commands) and corresponding responses and/or acknowledgements for accomplishing sending messages to the cellular network service (such as a connect request to access the cellular network), sending messages to the Notification Service 123 (such as alert messages), and receiving one or more messages or data (such as handshake and application acknowledgements, device settings and updates, and firmware updates). These sequences are programmed into the program memory 202 used to instruct the actions of the controller. FIGS. 12A-12E illustrate several example communication sequences, discussed hereinafter. The programming of the controller 201 according to predefined communication sequences enables another power saving technique in order to conserve battery power, namely providing a way for the controller 201 to recognize that a communication sequence is complete, the completion of which is used by the controller 201 as a trigger to place the cellular modem 203 and itself into a low-power mode (Power Saving Mode (PSM)) (step 216). In PSM, each of the controller 201 and cellular modem 203 turn off or place in a low-power state the features of their respective device that require higher power for operation. For example, the cellular modem 203 may disable the power to the antenna 204 (step 225) and then enter PSM (step 226) so that battery power is not consumed powering the antenna during periods when the controller 201 knows, by way of the programmed communication sequences, that it is not sending a message to, or expecting a message from, the network or Notification Service 123. For example, once the controller 201 completes a communication sequence (step 215) and instructs the cellular modem 203 and itself to enter PSM (step 216), it enters a very low power mode while awaiting an interrupt from the sensor 206.

The sensor 206 interrupts the controller 201 when sound/vibration is detected above the programmed threshold. When the controller 201 receives an interrupt, it exits from PSM (step 217), formulates an alert message (step 218) and wakes up the cellular modem 203. The controller 201 then executes a communication sequence (step 215) to notify the Notification Service 123 of the sensed event, and then cause the MDAD 200 to enter PSM once again (step 216).

The cellular modem 203, when instructed to exit from PSM, exits PSM (step 227) and enables its antenna (step 228). The cellular modem 203 then awaits AT commands from the controller 201 (step 223) and processes AT commands (step 224) in normal operating mode.

Returning to FIG. 3, in a preferred embodiment, the cellular network 110 is a Low-Power Wide Area Network (LPWAN) transmission module, which supports low-complexity, deep-coverage devices. By way of example and not limitation, exemplary LPWANs include LTE-M (including CAT-M1), EC-GSM-IOT, and NB-IOT cellular networks. In a preferred embodiment shown in FIG. 3, the LPWAN implements the 3GPP LTE-M (CAT-M1) specification and protocol, which support devices characterized by low-power transmission (max transmit power of 23 dBm), provides a low maximum system bandwidth (1.4 MHz), and allows a relatively low maximum peak data rate (1 Mbps). In this embodiment, the MDAD 105 is configured to transmit alert messages over a radio access network (RAN) 118 that supports LPWAN technologies. In the embodiment shown in FIG. 3, the radio access network 118 is a cellular LTE-M network operating in the licensed (i.e., regulated) spectrum. The LTE-M network operates over the same (or subset thereof) frequency bands as LTE) and implements 3GPP LTE-M specifications and protocols utilizing the existing LTE cellular infrastructure. The RAN 118 in the LTE cellular network includes what is referred to as the Evolved Universal Mobile Telecommunications System (E-UMTS) Terrestrial Radio Access Network (E-UTRAN), and a core all-IP network 119 referred to as the Evolved Packet Core (EPC). The E-UTRAN includes a network of cellular sites 111 (shown as 111a, 111b) providing areas of network coverage arranged in geographical "cells" across areas of Earth. Each cellular site includes at least one antenna mounted on a cell tower, which is designed to transmit and/or receive signals on a designated LTE-M frequency band. Within a given cell, transmitted signals adhere to minimum signal strength specifications to cover at least the entire area of the geographical cell. In practice, each cellular tower has multiple antennas sending and receiving over multiple LTE/LTE-M frequency bands, and each antenna is tuned to receive and/or transmit signals on various frequencies and in different directions. Each antenna is connected by wire or fiber optic cable to a base station (which in the LTE/LTE-M RAN is referred to as an Evolved Node B, eNodeB, or eNB). The base station, or eNB, is the primary interface for connecting subscribing user equipment devices (UEs) to other devices and services serviced by the particular LTE/LTE-M network service provider (often called the "carrier", such as commercial providers Verizon, AT&T, etc.). The base station is also the primary interface for connecting subscribing devices via networks of other providers (such as routing calls to UEs who subscribe to a different carrier than the sending UE, and to devices, machines and services on other networks (such as other RANs, packet switched and packet data networks). The eNB manages the radio interface between user equipment (UE) devices (such as mobile and/or remote LTE and LTE-M enabled devices) and the core network (referred to as the Evolved Packet Core (EPC)) which connects and routes messages between remote UEs subscribing to the LTE/LTE-M cellular network and UEs and other devices on networks of other carriers or packet data networks such as the Internet.

Referring again to FIG. 3, the radio access network (RAN) 118 provides connection between LTE-enabled devices and the core network 119. The core network 119, or EPC, is an all-IP (Internet Protocol) network that manages the interconnection of calls and data flow between devices connected to the RAN 118, to one another and to other networks 130 and/or packet data networks (PDNs) 120 and resources connected to the core network 119. The core network 119 forms the central control of the cellular network 110. Among other functions, the core network 119 manages authentication of user equipment (UE) (such as MDAD 105 and other UE such as cellular enabled mobile devices) requesting access to the cellular network 110, voice/data call and message control/switching/routing, allocating resources to meet subscriber quality of service levels, and setting up data traffic tunnels (known as bearers) between authenticated UEs to packet data network (PDN) gateways 115 for transfer of user traffic between the UEs and PDNs (such as the Internet 120).

In the LTE-M network, the core network (EPC) 119 includes a Mobility Management Entity (MME) 112, a Home Subscriber Server (HSS) 113, a Serving Gateway (S-GW) 114, a Packet Data Network Gateway (P-GW) 115. The MME 112 operates as the main control entity for the LTE radio access network (E-UTRAN) (which, in an LTE/LTE-M network, implements the RAN 118). The MME 112, with the assistance of a UE-connecting eNB 111, and a Home Subscriber Server (HSS) 113 that hosts network subscriber information, manages authentication of devices requesting access to the network 110. The MME 112 also manages control plane (Non-Access Stratum (NAS)) signaling, including mobility management, session management, and setup of tunnels, or "bearers" that carry user plane traffic. The MME 112 communicates with eNBs 111a, 111b, (and others not shown) in the radio access network 118 via the LTE S1-MME interface, while eNBs communicate with UEs via the LTE-Uu interface. When a UE requests access to the network, the eNB with greatest signal strength (usually the eNB nearest the requesting UE), along with both the UE and the MME serving the eNB, coordinate with each other to perform mutual authentication. In LTE networks, both LTE-enabled UEs and the LTE network follow well-known pre-defined LTE authentication protocols to ensure, from the UE's point of view, that the UE is accessing the network it thinks it is accessing and, from the network's point of view, that the UE has authorization to access the network and is who the UE says it is. The communication interfaces and protocols for LTE-M, including among others the LTE-UU, LTE-S1, LTE-S5 and SGi interfaces, are specified and published by 3GPP, available at www.3gpp.org, hereby incorporated by reference for all that they teach.

When an AED 102 (and more specifically, its MDAD 105) is authenticated, the MME 112 sets up an IP connection (or "session") between the MDAD 105 and a particular Packet Data Network (PDN) through which the MDAD 105 can communicate with the Notification Service 123 is accessible. Profile information associated with the authenticated AED 102/MDAD 105 is accessible through the Home Subscriber Server 113 (and/or a Profile Repository (not shown)), which stores default PDN IP address associated with the AED 102/MDAD 105. The AED 102/MDAD 105 can also specify a specific IP address during the access request. The MME 112 determines the IP address of the PDN with which the AED 102/MDAD 105 wishes to connect, using the default IP address from the AED 102/MDAD 105 profile information or from AED 102/MDAD 105 request information. The AED 102/MDAD 105 can have either a static IP address or may be dynamically assigned an IP address using standard Dynamic Host Configuration Protocol (DHCP) or other dynamic IP address allocation protocols. The session identifies the connection endpoint IP addresses, namely the IP address of the AED 102/MDAD 105 and the IP address of the PDN (also called the Access Point Name (APN)) through which the AED 102/MDAD 105 wishes to connect (presumably to use services).

Figure 6:
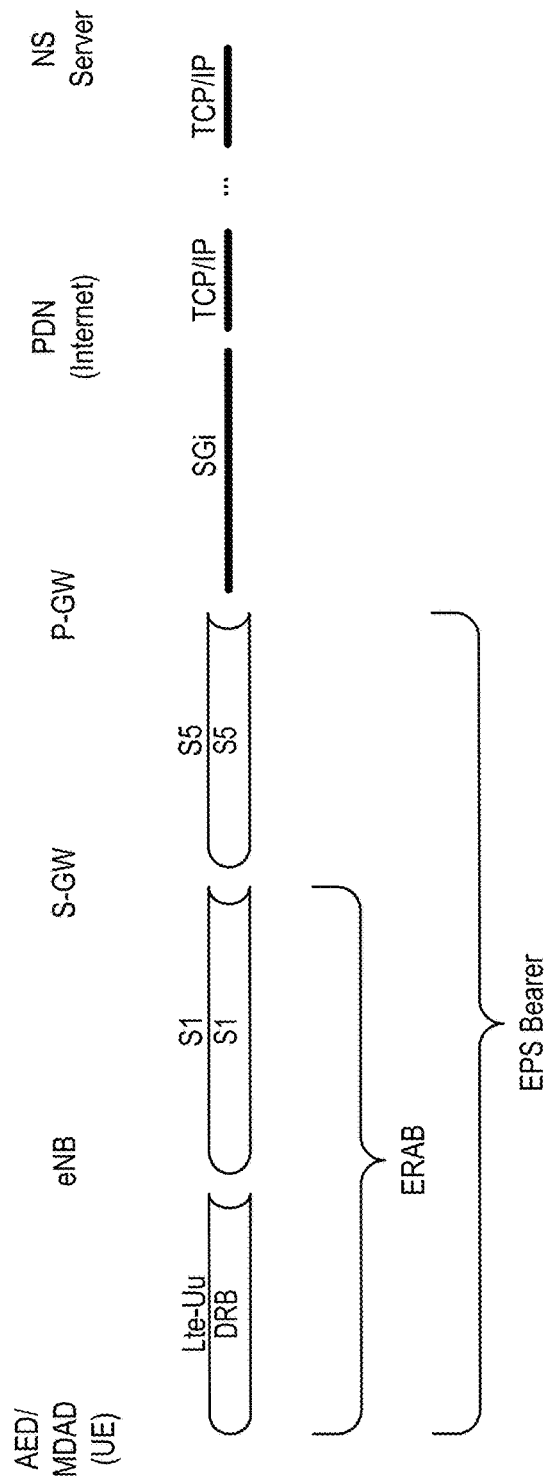
FIG. 6 is a diagram illustrating the bearers set up for a Long-Term Evolution (LTE) cellular network connection.

In conjunction with setting up the session, the MME 112 also sets up a default Evolved Packet System (EPS) bearer, which is a tunnel through which IP packets are transferred through the LTE network 110 between the AED 102/MDAD 105 and a PDN gateway (P-GW) that serves the destination PDN. With reference to FIG. 6, the default EPS bearer requires setting up of three different bearers due to the different communication interfaces between equipment located between the AED 102/MDAD 105 (UE) and P-GW (including the eNB, the S-GW and the P-GW). In the UE-to-P-GW direction, data flows from the UE to an eNB 111 via a data radio bearer (DRB) using the LTE-Uu interface, then from the eNB to the S-GW via the S1 interface, then from the serving gateway (S-GW) to the PDN Gateway (P-GW) using the LTE S5 interface. Accordingly three different bearers are set up to accommodate the different interfaces, which include a DRB (i.e., data tunnel) to deliver user data traffic between the UE and eNB using the LTE-Uu interface, an S1 bearer to deliver user data traffic between the eNB and S-GW, and an S5 bearer to deliver user data traffic between the S-GW and P-GW. The MME coordinates with the eNB, the S-GW and P-GW to set up these bearers. FIG. 3 details a small few cellular sites (eNBs) 111a, . . . , 111b, a single MME 112, S-GW 114 and P-GW 115, for the purposes of simplicity of illustration and explanation and not by way of limitation. It is to be understood that in practice, commercial LTE/LTE-M networks comprise many cellular sites 111 (eNBs), which may connect to several different MMEs, which are each connected to several S-GWs and P-GWs, serving different geographical locations of the overall cellular network. In an embodiment, the cellular network service provider through which MDADs gain access to the cellular network for subsequent transmission and receipt of messages over the Internet to and from the Notification Service is a 3rd-party commercial cellular network service provider that supports LTE-M, such as, by way of example only and not limitation, Verizon or AT&T.

LTE/LTE-M networks are all-IP networks, meaning that all user traffic is delivered by way of Internet Protocol (IP) packets. When an LTE-enabled UE, such as AED 102/MDAD 105 connects to the network, it is assigned an IP address, a session is set up, and data traffic bearers are set up between the UE device and a PDN gateway P-GW. The IP address assigned to the AED 102/MDAD 105 remains valid and the bearers remain connected until the device is detached from the network. That is, the session remains valid until the AED 102/MDAD 105 is detached from the network.

Figure 7A:
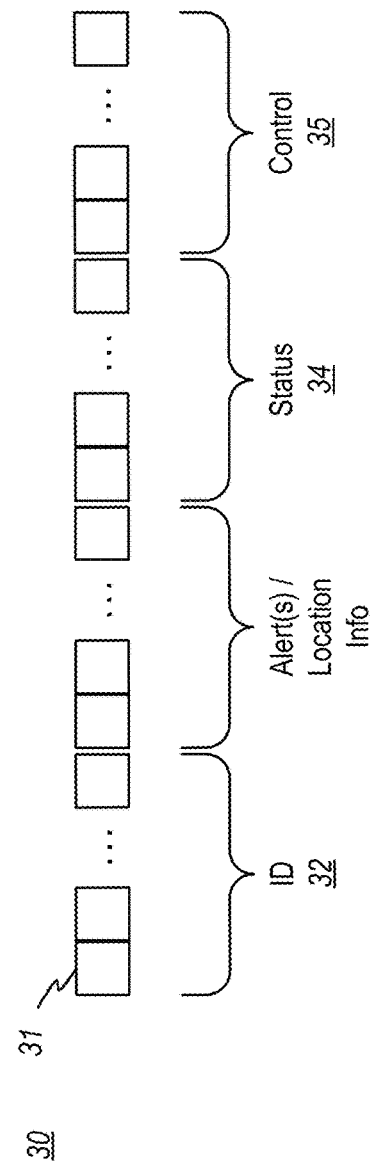
FIG. 7A illustrates an example format of a message payload for purposes of illustration and not limitation.

In the network system of FIG. 3, since the LTE-M network is an all-IP network, the movement detection and alerting device (MDAD) 105 uses the IP protocol for sending alerts. In particular, the MDAD 105 encodes an alert message (called the message payload) and formulates it into at least one IP packet containing an IP header and the message payload. FIG. 7A illustrates an example format of a message payload for purposes of illustration and not limitation. As illustrated, the message payload comprises one or more bytes 30 of bits 31. Groupings of the bits 31 correspond to encoded information. For example, one group 32 of bits 31 corresponds to encoded MDAD identification (ID) information. In an embodiment, the identification information includes a unique AED 102/MDAD 105 serial number and/or other AED 102/MDAD 105 identification information. Another group 33 of bits 31 corresponds to encoded alert information, which may include simple information such as an alert indicator indicating that the AED 102/MDAD 105 has moved, or which may include additional information such as but not limited to location information such as transmitted GPS coordinates of the AED 102/MDAD 105. Another group 34 corresponds to encoded status information, and yet another group 35 of bits corresponds to encoded control information. In an embodiment, the identification (ID) group 32 includes a plurality of bits that uniquely identifies the MDAD 105 to the Notification Service 123. In an embodiment, the ID group 32 comprises the serial number or an encoded version of the serial number of the MDAD 105. It may further include additional device information such as the IMEI and ICCID. Further in an embodiment, the alert group 33 comprises one or more bits indicating whether and which of one or more alert conditions are triggered. In an embodiment, the alert group 33 comprises one or more individual bits corresponding to each of a movement/motion/vibration detected condition and a battery low condition. The alert group 33 may comprises additional bits to represent the state(s) of additional monitored conditions, and further may include location information related to the movement such as but not limited to current GPS coordinates, most recent prior GPS coordinates, GPS coordinates of initial location of the AED 102, etc. Returning to the message payload, the status group 34 may comprise one or more bits indicating whether the MDAD is on or off, and the control group 35 comprises one or more bits of encoded control information. In an embodiment, the control information indicates whether the device is to be reset or needs firmware update(s).

Figure 7B:
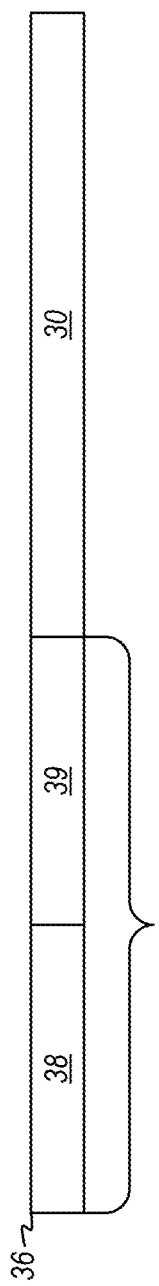
FIG. 7B illustrates the format of an IP packet transmitted from the MDAD to the nearest eNB in FIG. 3.
Figure 7C:
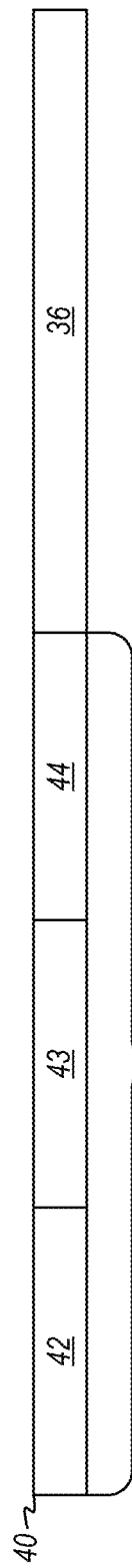
FIG. 7C illustrates the format of an S1 GTP IP packet.
Figure 7D:
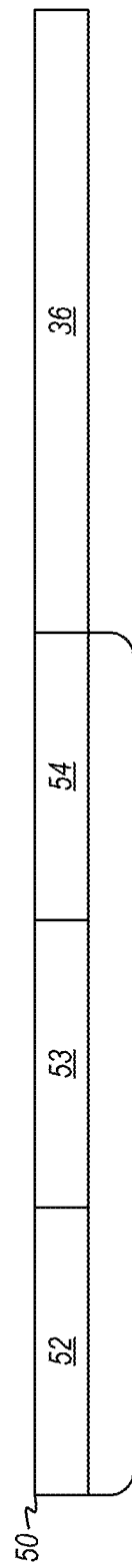
FIG. 7D illustrates the format of an S5 GTP IP packet.
Figure 7E:
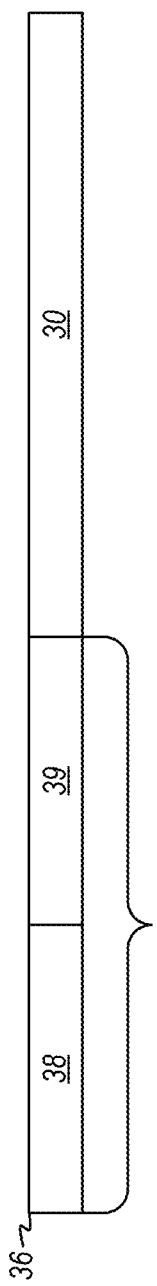
FIG. 7E illustrates an extracted IP packet.

FIG. 7B illustrates the format of an IP packet 36 transmitted from the MDAD 105 to the nearest eNB 111*a*. As illustrated in FIG. 7B, the IP packet 36 includes an IP header 37 and the message payload 30. The IP header 37 includes a destination IP address 38 and a source IP address 39, where the destination IP address 38 is the IP address of the Internet-enabled Notification Service 123 and the source IP address 39 is the IP address of the MDAD 105. Using the LTE-Uu interface, the cellular modem of the MDAD 105 transmits each IP packet to the nearest eNB 111*a* via the DRB bearer set up for that particular MDAD 105. With reference to FIG. 7C, the receiving eNB 111*a* receives each IP packet 36 and encapsulates each received IP packet with an S1 interface General Packet Radio System (GPRS) Tunneling Protocol (S1 GTP) header 41 to formulate an S1 GTP IP packet 40. The S1 GTP header 41 includes at least the destination IP address 42 of the destination Serving Gateway (S-GW) 114, the source IP address 43 as the IP address of the sending eNB, and an S1 Tunnel Endpoint Identifier (S1 TEID)) 44. The eNB then transfers the S1 GTP IP packet(s) 40 to a Serving Gateway (S-GW) via the S1 bearer via the S1 interface. With reference to FIG. 7D, the destination Serving Gateway (S-GW) 114 strips the S1 GTP header 41 from each S1 GTP IP packet 40 and encapsulates the stripped IP packet 36 into an S5 GTP IP packet 50, including an S5 interface GTP (S5 GTP) header 51. The S5 GTP header 51 includes at least the destination IP address 52 of the destination Packet Data Network Gateway (P-GW) 115, the source IP address 53 as the IP address of the S-GW 114, and an S5 Tunnel Endpoint Identifier (S5 TEID)) 55. The S-GW 114 then transfers the S5 GTP IP packet(s) 50 to the appropriate PDN Gateway (P-GW) 115 via the S5 bearer. The receiving P-GW 115 strips the S5 GTP header 51 from each packet 50 to extract the encapsulated IP packet 36 (FIG. 7E) and transfers the packet(s) onto the Internet 120 PDN via an SGi interface. Once the IP packet is on the Internet, it is routed to the destination IP address 38 of the Notification Service 123 through conventional IP and/or Ethernet routing using TCP/IP and DHCP.

The Notification Service 123 is connected to the Internet 120 and is responsive to requests addressed to its IP address (and appropriate port(s) and API calls) via the Internet 120, and further can transmit responses to requests and may send out its own requests to other devices at IP addresses on, or reachable via, the Internet 120 (and potentially additionally through a cellular network 110 to mobile cellular devices). The Notification Service 123 is an application executing on a computer system 122 that is accessible via a web server 121 connected to the Internet 120. The computer system 122 may be a central processing unit executing Notification Service program instructions stored in local or remote computer-readable memory. The Notification Service 123 may be a web-enabled service. In particular, the web-enabled service may be an instance of a Notification Service application executing in the Cloud, such as an E2C instance running on an Amazon Web Services (AWS) cloud web hosting platform.

Figure 8:
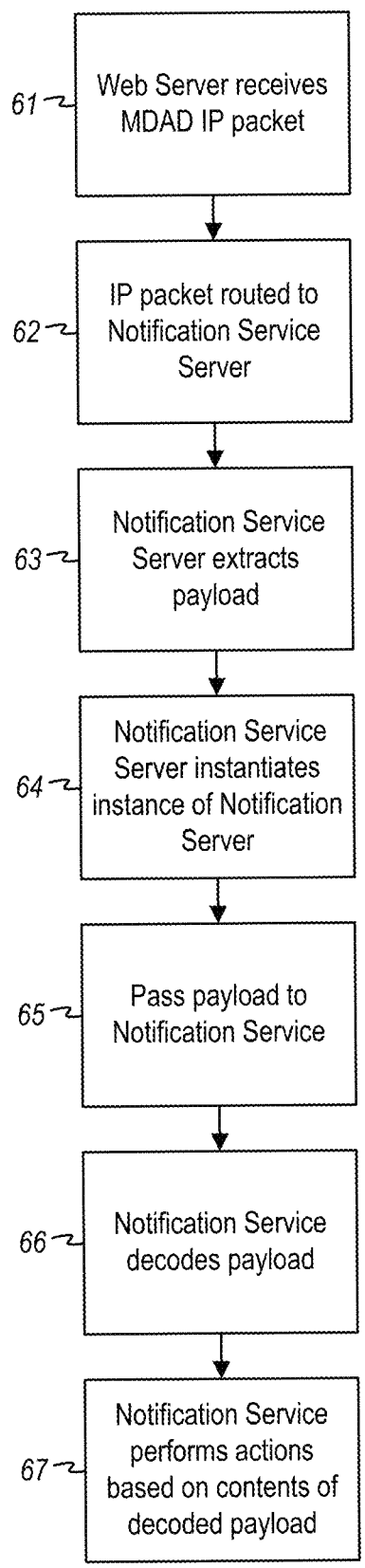
FIG. 8 is a flow diagram illustrating operation of an exemplary embodiment of the Notification Service.

FIG. 8 is a flow diagram illustrating operation of an exemplary embodiment of the Notification Service 123. As a preliminary step, a message in the form of an IP packet 76 is transmitted from a P-GW 115 over the Internet 120 with the destination IP address of the Notification Service Server 122 and is received first by a Web Server 121 (step 61), routed to the Notification Service server 122 (step 62), which extracts the payload of the received message (step 63), instantiates an instance of the Notification Service 123 (step 64), passing the payload 76 to the Notification Service 123 (step 65) via a Notification Service API. The Notification Service 123 decodes the message payload 70 (step 66) and performs one or more actions based on the contents of the payload (step 67). In particular, the Notification Service 123 performs a series of appropriate steps according to predefined programming instructions. The Notification Service 123 performs one side of at least some of the Communication Sequence(s). For example, it performs the Notification Service steps outlined in the Command Sequences, detailed hereinafter in connection with FIG. 12.

In an embodiment, the Notification Service 123 is software hosted on a computer system, such as a Cloud computing provider. Preferably, the Notification Service 123 provides an Application Programming Interface (API) by which client devices can access the Notification Service 123. In an embodiment, the hosting computer system instantiates an instance of the Notification Service 123 upon receipt of a proper API call to the Notification Service 123. In other words, when a web browser or other software or another system generates a Uniform Resource Locator (URL) request containing the correct IP address of the hosting computer, along with the correct path to the directory containing the executable of the Notification Service 123, and the API call is formatted correctly and contains valid parameters, the API call automatically instantiates an instance of the Notification Service 123. In an embodiment, the Notification Service 123 is hosted on a computer that is accessible via the Internet. For example, the Notification Service 123 may be a cloud-based service that is hosted on a server such as an AWS server connected to the Internet. In an alternative embodiment, the Notification Service 123 may be a service that runs on an internal network of a closed network system.

Figure 9:
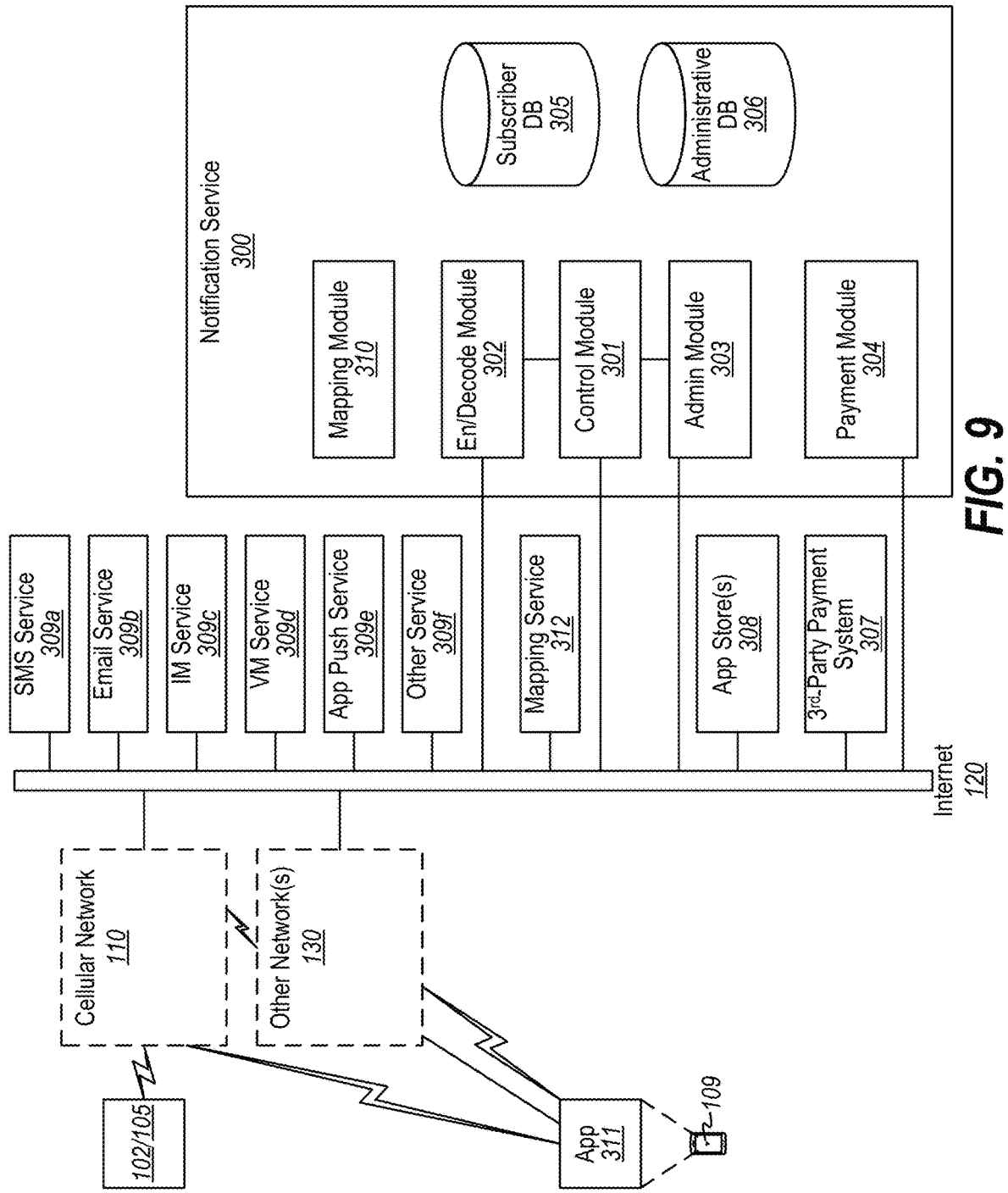
FIG. 9 is a network diagram of the architecture of the Notification Service.
Figure 10:
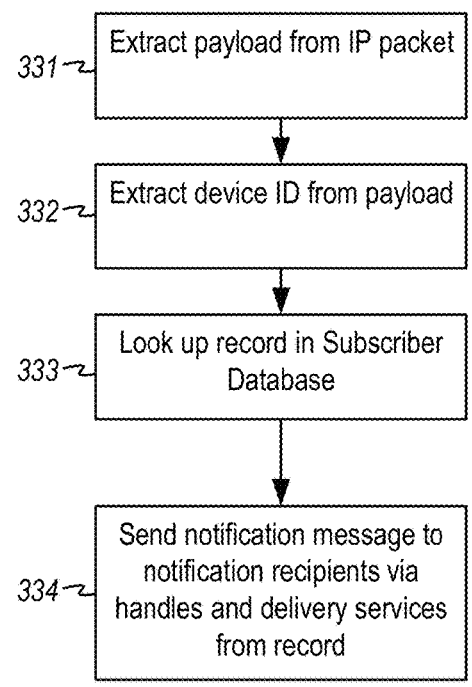
FIG. 10 is an operational flow diagram of exemplary steps performed by the Notification Service.

FIGS. 9 and 10 show a more detailed diagram of the architecture (FIG. 9) and operation (FIG. 10) of the Notification Service 123. In this environment and embodiment of the Notification Service 300 for implementing the Notification Service 123. As shown in FIG. 9, an embodiment 300 of Notification Service 123 from FIG. 3 comprises a plurality of software modules, including a central control module 301, an encode/decode module 302, an administrative (Admin) module 303, a payment module 304, a subscriber database 305, a code database 306, and, optionally, a mapping module 310. Each of the modules comprises computing resources and computer-readable storage memory. For example, each module 301, 302, 303, 304, 310 may comprise a service or application or program comprising program instructions and executed by a processor such as a Central Processing Unit (CPU), microprocessor, cloud computing resource (such as an Amazon Web Service E2C instance), etc. Each of the databases 305 and 306 comprises computer-readable storage memory and may be implemented as a managed system (DBMS), local storage, an Amazon Web Services S3 bucket, etc.). The Notification Service 300 is connected to the Internet 120 through which it may communicate with one or more 3rd-party payment system(s) 307, app store(s) 308, mapping service(s) 312, electronic delivery services such as an SMS texting service 309a, an email service 309b, an Instant Messaging (IM) service 309c, a VoiceMail service 309d, and App Push Notification service 309e, or other Internet-enabled services 309f.

The encode/decode module 302 decodes messages received from MDADs 105 that are routed to it from the AED 102/MDAD 105 through the Internet 120 from the P-GW of the cellular network 110 (step 331). Decoded messages are passed from the encode/decode module (specifically the decode portion of the module) to the control module 301 to process the message in accordance with predefined instructions as set forth herein, for example as described in connection with steps 17-22 of FIG. 2.

The encode/decode module 302 (and specifically the encode portion of the encode/decode module 302) also encodes messages and data to be sent from the Notification Service 300 to the AED 102/MDAD 105 into a packet payload in a format that will be decodable by the AED 102/MDAD 105 when received (step 332) and formats the packet payload into one or more IP packets (step 333) for routing through the Internet to the cellular network 110 (step 334) for delivery therefrom to AEDs 102/MDADs 105. The central control module 301 operates as the central controller for the Notification Service 300 and offers one or more Application Programming Interface(s) (APIs) to allow other modules, services and devices connected to the Internet to communicate with the Notification Service 300.

The Admin Module 303 provides access to profiles of subscribers to the Notification Service 300 and methods for setting up subscriber accounts, adding/modifying/removing AED 102/MDAD 105 IDs and associated notification recipients. Information including subscribing device IDs and notification recipients is stored in Subscriber Database 305.

Figure 11:
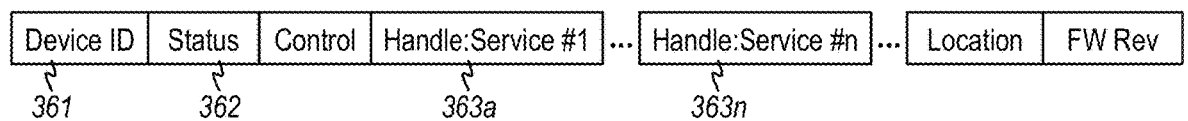
FIG. 11 is a format diagram of a record stored in the Subscriber database.

FIG. 11 illustrates an example record 360 stored in the Subscriber Database 305. Generally, at least one record is stored for each MDAD 105 that is monitored by the Notification Service 300. A typical subscriber database 305 will store thousands or hundreds of thousands or more records, corresponding to unique MDADs 105. As illustrated, a record 360 for a monitored MDAD 105 includes at least a device identifier 361 and one or more notification recipient delivery service handles (username, phone number, user or device identifier, etc.) and corresponding delivery services through which a message can be delivered to one or more person(s) corresponding to such handle(s) (see 363a, 363b, . . . , 363n). In an embodiment, the identifier 361 comprises the serial number of the device 105. In an embodiment, each notification recipient information 363a, 363b, . . . , 363n comprises a delivery service handle associated with a notification recipient, along with an identifier of the corresponding delivery service through which the notification recipient associated with the handle is to be notified. For example, the delivery service handle may comprise an email address and the delivery service associated therewith would be an email notification service, such as an SMTP mail server. As another example, the handle maybe a mobile device phone number, and the associated service may be an SMS texting service. Other exemplary notification information may include without limitation, a mobile device phone number and associated app push notification service, and instant message (IM) handle and associated instant messaging service, and a phone number and associated VOIP mail service.

Subscribers to the Notification Service 300 may interact with the Notification Service 300 through a website or a downloadable App 311 running on their device 109 (such as but not limited to 109a-109e shown in FIG. 1), which may be a mobile device such as a smartphone, a tablet or laptop, or may be a desktop, terminal connected to a server or other computer, etc. The app 311 may be downloaded to the user's device 109 from a device-accessible app store, such as the Apple App Store, Google Play, or other app stores through which apps can be selected and downloaded. Apps may be provisioned in the app stores from the code database 309. The app 311 runs locally on the user's device. Alternatively, the user interface comprises a graphical user interface (GUI) presented on a web page in a web browser running on the device 109.

The Admin Module 303 may further comprise code management tools which allow an administrator to manage app and firmware versions and to designate firmware upgrades which may be stored in a code database 309. Furthermore, the Admin Module 303 may be configured to allow a vendor or manufacturer of the AED 102/MDAD 105 devices to keep track of firmware versions of the respective devices in the field, and control deployment of firmware upgrades to such devices. For AEDS 102 with low-power MDADs 105, a firmware upgrade may be deployed only after the MDAD 105 contacts the notification service 300. This protocol allows the AED 102/MDAD 105 to conserve power since it does not have to power up occasionally to listen for messages from the Notification Service 123. In other embodiments the AED 102/MDAD 105 may be programmed to check in with the Notification Service 123 or manufacturer on a timed schedule to receive any firmware upgrades.

The subscriber database 305 may further include firmware version information and other status and control settings 362 that may be set by the administrative module 303 to indicate to the control module 301 when one or more control operations need to be performed on a given MDAD 105, which is especially useful for MDADs 105 configured for low-power mode so that the Notification Service 300 is programmed to update the MDAD 105 firmware when such MDAD 105 next contacts the Notification Service 300. For example, the subscriber database 305 may include one or more bits indicating whether one or more firmware modules on the corresponding MDAD need to be upgraded or changed to a different version of firmware. The administrative database 306 comprises computer-readable storage memory which stores one or more different versions of firmware, apps for the App Store(s) 308, and other administrative data, program data, and information. For example, the administrative database 306 may include app code and various versions thereof of an app that may be downloaded to an app store 308 and made available to subscribers to the Notification Service 300 through such app store 308 to download to their own app-enabled device 109 (such as a smartphone, a tablet, a laptop, or desktop), and execute their own instance 320 of the app in such local device(s) 109. For example, the Notification Service 300 may make available one or more apps such as and iOS app for Apple devices such as iPhones and iPads, and an Android app for Google Android devices. These apps may be made available through the Apple store or Google App Store. End user devices communicate with the app using conventional app technology such as made available through iOS and Android.

The Control Module 301 provides an API through which user apps 311 can communicate with the Notification Service 300 and configure their user profile, notification recipient information, and the settings for their own AED 102/MDAD 105. Users connect to the Notification Service 300 through the app 311 running on their local device 109, which connects to the Internet directly through WiFi, a LAN (via Ethernet), or indirectly through a cellular or other network 130. The app 311 provides prompts for the user, and radio buttons and other widgets to allow the user to control device settings or opt in or out of various Notification Service settings. As an example, the app 311 may provide a slider that allows a user to set the sensitivity settings of the MDAD (which may correspond directly to the sensor thresholds from which alerts are generated, or which may be controlled via logic in the MDAD firmware or in the control module 300). Communication between the app 311 and control module 301 are routed using conventional TCP/IP over the Internet 120.

When a user or owner of an AED 102/MDAD 105 subscribes to the Notification Service 300, the user enters the subscriber information, including subscriber details such as contact information, notification recipient information including delivery service handles and associated delivery services to use to notify notification recipients, and payment information. During registration with the Notification Service 300, the user may be required to submit a payment for subscribing to the services. Accordingly, the Notification Service 300 may also include a Payment Module 304. The Payment Module 304 may either manage payment from a subscriber directly or may handle communication with a $3^{rd}$-party payment processing system 307 to process payments.

One of the main purposes of the Notification Service 300 is to alert subscriber-designated notification recipients of activity or movement of AEDs 102/MDADs 105. To this end, when the control module 301 processes an alert message that it determines requires generation of a notification to one or more notification recipients, it accesses the subscriber database 305 to look up the notification recipients and corresponding delivery handles and associated delivery services, formats messages appropriate to the particular delivery services, and sends the message(s) to the respective delivery services via the Internet 120. Each delivery service includes an Internet-enabled delivery service running on computer systems or other hardware that is connected to, and accessible via, the Internet 120. For example, the Notification Service 300 may utilize the service(s) of one or more SMS text services 309a, one or more email services 309b such as SMTP services, one or more instant messaging services 309c, one or more text-to-voice or other voice mail messaging services 309d, one or more app push notification services 309e, and one or more other Internet-enabled messaging services 309f. Such services adhere to conventional TCP/IP protocols for passing messages thereto.

In an embodiment, the Encoder/Decoder module 302 is the initial point of entry to the Notification Service 300 of messages issued from MDADs 105 and is the exit point from the Notification Service 300 for messages going to AEDs 102/MDADs 105. Each message payload coming from an MDAD 105 is in an encoded format, for example as discussed in connection with FIG. 7A. Referring to FIG. 10, the Encoder/Decoder module 302 (specifically, the Decoder portion of the module 302) extracts the message payload (step 331) and decodes the message bits into a format or other data usable by the control module 301. Given the decoded payload, the control module 301 extracts the device ID of the AED 102/MDAD 105 from the payload (step 332), looks up the record corresponding to the device ID from the Subscriber database 305 (step 333). Based on the decoded information generated by the Decoder module 302 and information stored in the corresponding record, the Control Module performs one or more actions, such as sending a notification message to notification recipients to notify them of the alert condition at the AED 102/MDAD 105 (step 334). In an embodiment, these actions correspond to the Command Sequences, discussed hereinafter in connection with FIGS. 12A-12E.

FIGS. 12A-12E illustrate a set of exemplary Command Sequences executed by the MDAD, including an Initial Connection Command Sequence (FIG. 12A), an alert message Command Sequence (FIG. 12B), a Set Device Settings Command Sequence (FIG. 12C), an Alarm Sequence (FIG. 12D) and a Pause Sequence (FIG. 12E). These command sequences are executed by the MDAD 105 in cooperation with the Notification Service 123. As illustrated in FIG. 12D, the Alarm Sequence is what triggers the Notification Service 107 to notify notification recipients that the AED 102/MDAD 105 has been moved. In an embodiment, the alarm sequence is initiated when the Trigger bit in the decoded message payload is set to a value that corresponds to a trigger having been triggered. When the control module 301 in the Notification Service 300 detects that the Trigger bit of the message payload is set to the trigger value (for example Trigger=1 for "true"), then the control module 301 accesses the subscriber record associated with the AED 102/MDAD 105 in the subscriber database 305, and for each notification recipient handle associated with device ID, it formats a notification message appropriate for corresponding delivery service (e.g., a human readable text or email message), and sends the formatted notification message to a delivery address indicated by the handle using corresponding delivery service.

As earlier mentioned, the AED 102/MDAD 105 may include a location information transceiver 209 which receives location information from a satellite system such as GNSS or from another geolocation system such as a LoRa, cellular or WiFi network, and extracts location information such as longitude and latitude, GPS coordinates, or other labeled geolocation identifier(s). In an embodiment, the location information transceiver 209 comprises a GNSS transceiver which receives Global Positioning System (GPS) signals from the Global Navigational Satellite System and extracts the GPS coordinates. When location information is collected, the controller 201 may store the location information in the computer memory 202 and/or may compare it to previously stored location information to determine whether the AED 200 has moved from the location indicated by the previously stored location information. Thus, in an embodiment, the MDAD 105 may include only the location information transceiver 209 and not the accelerometer 206a, while the movement detection device 206 may be a processor such as a CPU and programming instructions which implement the location comparison between a previously stored location value and a current location value based on the location information extracted from the location transceiver 209 via a transceiver antenna 209a. In an alternative embodiment, the MDAD 105 includes both the accelerometer 206a movement detection device 206 and the location transceiver 209, whereby the AED 200 is placed in a low-power mode while the accelerometer 206a monitors and detects initial movement of the AED 200 and further where upon detection of the initial movement of the AED 200 by the accelerometer, the controller 201 turns on full power mode to the controller 201, cellular modem 203 and location transceiver 209 to obtain current location information and send the current location information as part of the message payload when sending the alert message to the Notification Service 123. Thus, if and when the AED 200 is moved, the movement will trigger an alert message to the Notification Service 123, whereby the alert message will indicate not only that the MDAD 105 of the AED 200 has detected movement of the AED 200, but also indication of current location information of the AED 200.

When location information 33 is included in the alert message 30, the control module 301 may pass the location information extracted from the message 30 to a mapping module 310. The mapping module 310 may combine the location information with a map image or map file or mapping information to generate a visual map image for display on a web page or in an app 311, in order to provide a visual indicator indicating the location of the AED 200 on the map. In an embodiment, the end user app 311 displays the visual map with visual indicator of the location of the AED 200.

If the MDAD 105 is not equipped with the location information transceiver 309, location information may be entered manually using the app 311 or a web portal (not shown) which allows the person installing the AED 200 in a location to enter labeled information (such as street address, location within building, manually determined location information, etc.). Alternatively, the person installing the AED 200 may use a GPS-enabled device such as their smartphone to determine location information. For example, the user of the app 311 on a smartphone can use native device code (for either IOS or Android or another device operating system) to obtain longitude and latitude. The end user typically must accept the use of location services for the feature to be enabled. Once the end user enables the feature they can then use a mapping service such as a "Google Maps" overlay which will send the longitude and latitude via an API which will then return and display the location on a map on the screen of the user's device. The end user may also choose to use Google Maps without an API call and set a "map pin" manually which can be stored in the subscriber database associated with the AED 102/MDAD 105 ID to see the last known static location.

Figure 13:
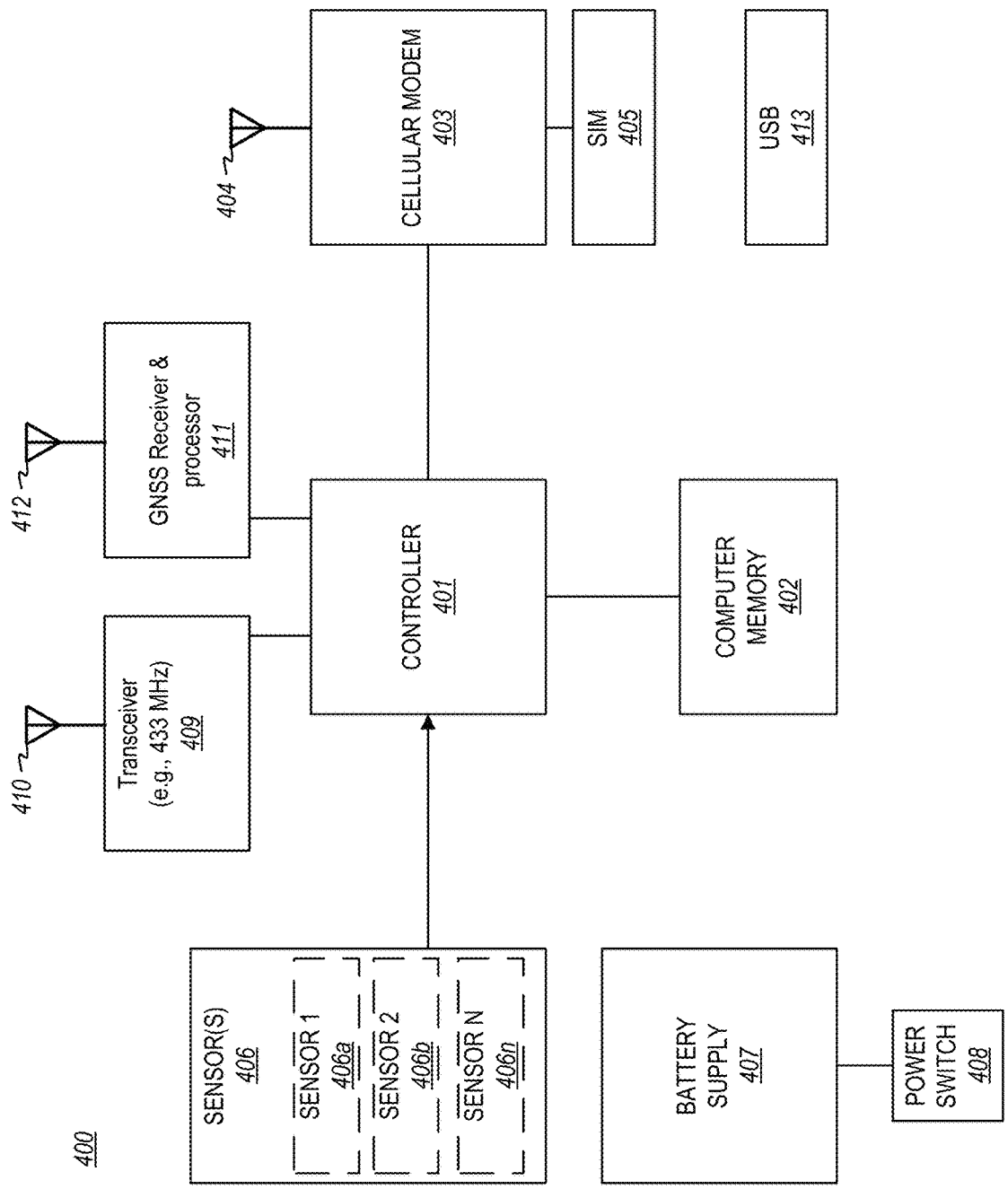
FIG. 13 is a block diagram of a sensor alert notification device (SAND)

It will be appreciated that a more expansive AED tracking system can be implemented using the MDAD. FIG. 13 is a block diagram of a sensor alert notification device (SAND) 400. In this embodiment, the SAND 400 includes a controller such as but not limited to a microprocessor 401, computer readable storage memory 402, a cellular modem 403 with antenna 404, a SIM 405, a battery supply 407 and a power switch 408. Additionally, the SAND 400 may include one or more sensors 406a, 406b, 406n (collectively 406) that sense, and/or sense and process, an environment, to respectively detect a respective predefined condition and to alert the controller 401 upon detection of such predefined condition. Sensors 406 may be directly electrically coupled to the controller 401. For example, each of sensors 406 may have a corresponding alert output that electrically connects, directly or indirectly through additional circuitry, to one or more interrupt ports of the controller 401. Corresponding interrupt service routines within the program code of the controller 401 (which may be stored in memory 402) implement control logic for processing the alert, decoding the alert (if necessary), determining whether to send an alert message to an external notification service (such as Notification Service 123) in cooperation with the cellular modem 403 over an LPWAN. In an embodiment, no sensors 406 exist on board the SAND 400 (i.e., SAND 400 communicates with remote sensors 421 (see FIG. 14)). In an alternative embodiment, one or more sensors 406 are implemented on board the SAND 400.

Figure 14:
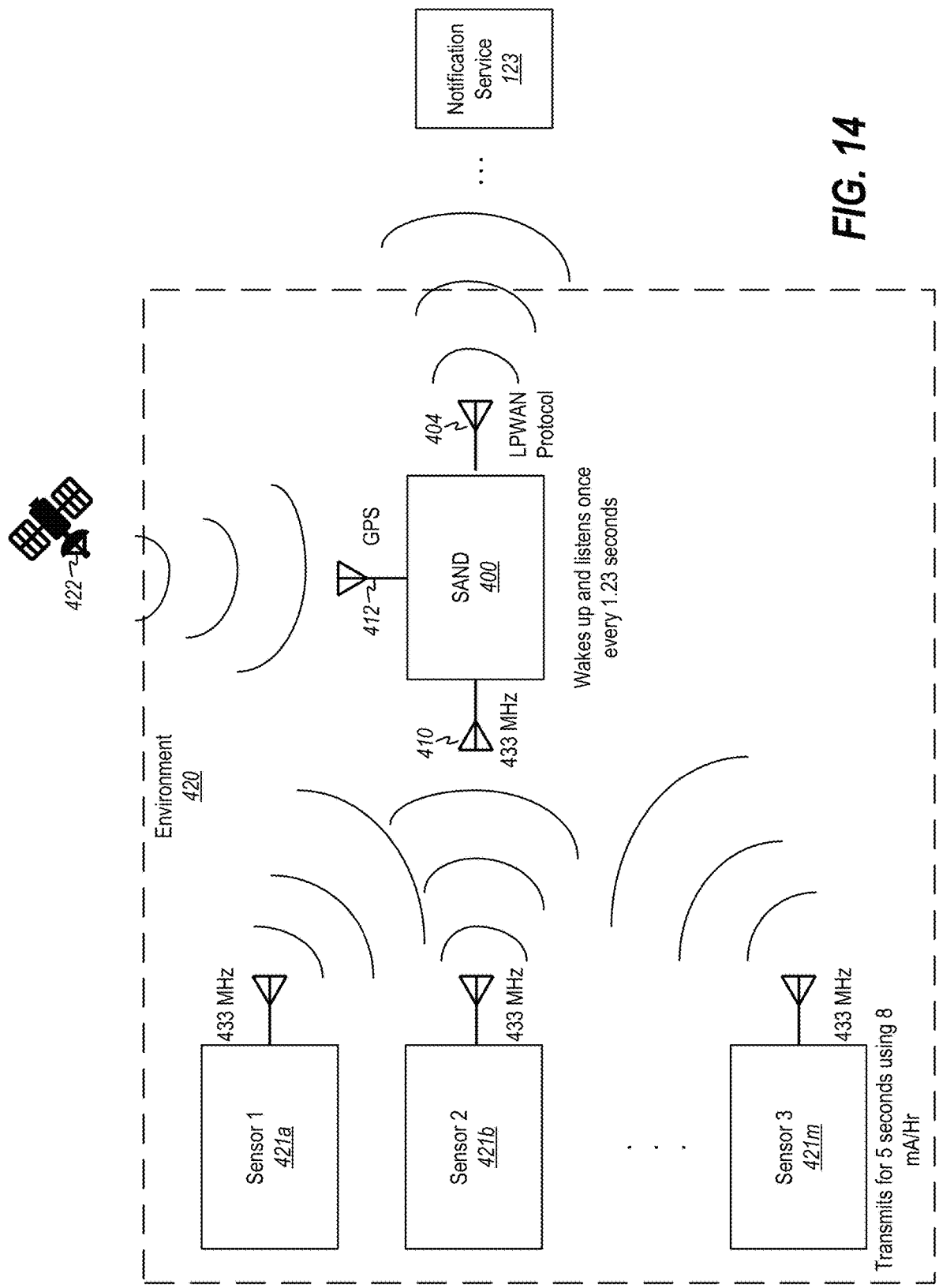
FIG. 14 is a block diagram of a network environment in which a SAND may operate.

In an embodiment, the SAND 400 includes a local area transceiver 409, such as a 433 MHz transceiver, equipped with an antenna 410. With reference to FIG. 14, in an embodiment where the SAND 400 is equipped with a local area transceiver 409, the SAND transceiver 409 listens for signals from remote sensors 421a, 421b, 421m (collectively 421) located in the proximate environment 420 where the SAND 400 can pick up the LPLR signal(s) transmitted over the local area antenna(s) from the sensor(s) 421. In an embodiment, the SAND local area transceiver 409 (FIG. 13) is a receiver only, and only receives signals from the remote sensors 421 and does not communicate out to the remote sensors 421. In an embodiment, any number of remote sensors 421 may transmit alerts and the SAND may process alerts sent by any number of remote sensors 421. In this way, the SAND 400 can be configured to operate as a gateway for the remote sensors 421 to the Notification Service 123 for sending out alert notifications to notification recipients.

FIG. 15 depicts an example high-level format of a message that is transmitted by a remote sensor 421a, 421b, 421m to the SAND 400. As illustrated, the message comprises a plurality of binary bits, and includes a number of bits referred to as a pilot period 432 which the transceiver 409 on the SAND 400 uses to trigger the start of a potential message. The message format 430 further includes a synchronization period 433 comprising a known pattern of bit values used by the SAND 400 to synchronize the receiver with the incoming data stream. Following the synchronization period 433, in an embodiment, the message contains an address period 434, where the sensor broadcasts an address recognizable by the SAND 400. A number of data periods 435a, . . . , 435n follow (collectively, 435). The data periods 435 may collectively comprise sensor identification data (such as but not limited to a sensor number), the type of the sensor, status and/or control bits from which the controller 401 can identify which sensor is sending the message, what its status is, and/or whether any control operations (such as updating firmware, notifying of a low battery condition, etc.) need to be performed. Following the data periods 435, the SAND 400 transmits a Post code 436 which indicates that the communication is complete.

In an embodiment, the SAND 400 comprises a Global Navigation Satellite System receiver (and processor) 411 (such as one capable of acquiring and processing signals from the Global Positioning System (GPS), GLONASS, Galileo, BeiDou and other regional satellite navigation systems) to determine location of the SAND 400 using time signals transmitted via satellite radio waves along a line of sight. In an embodiment, the GNSS receiver 411 is integrated into the same integrated circuit as the cellular modem 403. For example, in one embodiment, the cellular modem 403 and GNSS Receiver 411 are implemented using a Quectel BG96, as detailed previously. In an embodiment, the controller 401 may turn on the GNSS receiver 411 periodically to acquire the current position of the SAND 400. In an embodiment, when an alert message is formulated and sent to the Notification Service 123, the controller obtains the current (or most recent) geo-spatial position of the SAND 400 as acquired by the GNSS Receiver and processor 411, and includes the current (or most recent) location coordinates in the payload of the alert message that it sends to the Notification Service 123. The Notification Service 123 may use the geo-spatial position coordinates to as data input to its control logic. Alternatively, the Notification Service 123 may include the geo-spatial position coordinates in its message to notification recipients.

As previously mentioned, an important consideration in the implementation of the MDAD or SAND and other system elements may be the limited power supply available for powering the MDAD/SAND due to its stand-alone battery power supply. In order to maximize the life of the MDAD in the field, the MDAD may be configured to implement several additional power saving features. In an embodiment, the controller 201 is programmed to determine whether, and how often, to send an alert message to the Notification Service 123 when the movement detection device 206 is triggered by sound/vibration above its programmed threshold. For example, in an embodiment, the controller 201 may be programmed to send an alert message to the Notification Service 123 every time it is interrupted by the movement detection device 206. However, for situations where detected sound is above the programmed threshold for long periods of time, this may generate many alert messages that provide no additional information. In an alternative embodiment, the controller 201 may be programmed not to send an alert message to the Notification Service 123 if it has already sent an alert message within a programmed amount of time. It may further be programmed to change the rate at which it sends alert messages. For example, when the controller 201 receives a first interrupt, it may immediately send an alert message to the Notification Service 123. Upon receive of a second interrupt within a given period of time from the first interrupt, it may delay sending another alert message until a certain amount of time has passed and the condition still exists, and/or may gradually increase the delay in sending additional alert messages if it continues to receive interrupts that appear to be a result of the same condition causing the first interrupt (e.g., a prolonged sound or vibration) based on proximity in time of the interrupts.

Determination of whether to send an alert to the Notification Service 123 may vary depending on the purpose and application of use of the MDAD/SAND. In an embodiment, the MDAD/SAND controller sends an alert message for every alert generated by a sensor. In an embodiment, the MDAD/SAND controller sends an alert upon the satisfaction of one or more additional conditions (for example, a certain amount of time must pass before sending a next alert). In an embodiment, once an alert is sent, if the sound signal or other sensed condition continues without cease for a certain duration of time, the MDAD/SAND sends only one or a small few alerts. If the sound signal or other sensed condition ceases, in an embodiment, the MDAD/SAND may send another alert indicating cessation of the sound signal. In general, the MDAD/SAND controller may be programmed to send as many or few alert messages to the Notification Service 123 as meets the requirements of the application and purpose for which the MDAD/SAND is installed. For example, it may be sufficient to alert the Notification Service 123 a single time upon receipt of a first alert by a sensor and then ignore further alerts. In a different application, it may be better to require a set number of alerts from a given sensor before alerting the Notification Service 123. In yet another application, it may be desired, once an alert message has been sent to the Notification Service 123, to send an alert upon cessation of the condition that caused the alert. In accordance with the invention, many different scenarios in the alerting scheme are feasible and contemplated for use with the MDAD/SAND, and any exemplary embodiments described herein are not intended to be limiting.

In an embodiment, upon receiving an alert message, the Notification Service 123 decodes the alert and extracts the device identifier and alert code and/or other message information from the alert message. Depending on the specific alert code and/or other message information, the Notification Service 123 may determine whether to send a notification message to the notification recipients associated with the sending device. In an embodiment, the Notification Service 123 sends a notification message to all notification recipients for every alert message it receives from the MDAD/SAND. In an alternative embodiment, the Notification Service 123 may process the alert code and send a notification message only under certain conditions. For example, if the Notification Service 123 determines it has received an identical alert code within a predetermined time period before the receipt of the present alert code, it may be programmed to ignore the later-received alert message from the MDAD/SAND until the predetermined time period has passed. Alternatively, the Notification Service 123 may continue to send alert notification messages to the notification recipient(s) upon receipt of repeat alert notifications from the MDAD/SAND, but the controller may increase, or gradually increase, the time between sending notification messages to the notification recipients. In this way, notification recipients will not be overwhelmed with notification messages that alert to the same ongoing condition.

In an embodiment, the MDAD 200 may send a status message to the Notification Service 123 on a programmed schedule. The status message may be used to inform the Notification Service 123 that the MDAD 200 is operating and is able to communicate with the Notification Service 123. The Notification Service 123 may be programmed to expect a status message from the MDAD 200 according to programmed timing. For example, the MDAD may send a status message once every 12 hours or more (or less if desired). The Notification Service 123 may be programmed to send a notification to the notification recipients if it expects a status message from the MDAD 200 and does not receive a status message within a defined time period after missing one or more expected status message(s). This device status updates feature (or "device heartbeat" feature) enables notification recipients to know whether the MDAD 200 is powered on and in communication with the Notification Service 123, or whether a communication problem between the MDAD 200 and Notification Service 123 exists. The device heartbeat can be set at a rate such that the device checks in with the Notification Service 123 once every several hours, day(s), etc. or other (potentially user-configured) period of time. Rather than checking in with the network every 1.2 seconds (to let the nearest tower know where the device is), the heartbeat can be set to a much longer period of time to enable it to conserve power. The MDAD 200 need only register with the network, then go into a standby mode and need not connect to the tower until it needs to send a message.

In an embodiment, the MDAD 200 includes an optional GPS module 208 with a GPS antenna 209. The GPS module 208 may be implemented as a separate integrated circuit or could be embedded within the cellular modem IC 203. For example, the Quectel BG96 CAT-M1/NB1 & EGPRS Module optionally includes a GPS receiver and GPS processing circuitry for receiving GPS data from the Global Positioning Satellite System (GPSS). The controller 201 of the MDAD 200 may be configured to retrieve GPS coordinate data of the MDAD 200. In an embodiment, the MDAD 200 sends GPS coordinate data to the Notification Service 123. It may send the GPS coordinate data along with each alert message. In an alternative embodiment, the controller 201 may be programmed to track the GPS coordinate data, determine whether the MDAD 200 has moved from a previous location, and then track the GPS coordinate data, and transmit the GPS coordinate data to the Notification Service 123 on a programmed time basis.

In the illustrative embodiment described heretofore, the cellular network 110 is an LTE-M cellular network implemented in accordance with the Third Generation Partnership Project (3GPP) standards-based LPWAN technology, LTE-M (also known as LTE CAT-M1), which has a maximum channel bandwidth of 1.4 MHz, a maximum data rate of 1 Mbit/s, and operates in either full or half duplex mode (i.e., can transmit and receive simultaneously in full duplex mode, or can only transmit or receive at any given time in half duplex mode). In an alternative embodiment, the Low-Power Wide Area Network (LPWAN) could be implemented according to the Third Generation Partnership Project (3GPP) standards-based LPWAN technology, NB-IoT (Narrow Band Internet of Things, also known as CAT-NB1 or CAT-M2), which has a maximum channel bandwidth of 180 kHz, a maximum data rate of 250 Kbit/s, and operates only in a half-duplex mode. In another alternative implementation, the cellular network could be implemented according to the Global System for Mobile Communications Association (GSMA) standards-based LPWAN technology known as Extended Coverage Global System for Mobile (EC-GSM), (also called EC-GSM-IOT), which also operates in the licensed spectrum (on the 900 MHz and 1.8 GHz frequency bands) and implements EC-GSM protocols utilizing the existing GSM networks and GSM cellular to Internet infrastructure.

Some of the specifications for each of the LTE CAT-M1, CAT-NB1 and EC-GSM-IoT standards are given in FIG. 16, illustrating that each type of network requires different hardware (to transmit on different frequencies, with different bandwidth, data rates and modulation schemes, and to achieve perform different variations of duplexing and low-power modes). The particular type of cellular network that may be used for transmission of an alert message between a given MDAD 5 and the notification service 7 may depend on various factors, including availability of a given type of cellular network in the geographical region where the MDAD is installed, whether the MDAD is authorized to access an available cellular network, how much data and how quickly such data needs to be transmitted to the notification service, etc.

TABLE 1

|  | CAT-M1 | NBIoT | EC-GSM-IoT |
| --- | --- | --- | --- |
| Deployment Coverage | LTE 155.7 dB | LTE 164 dB | GSM 164 db, with 33 dBm power class, 154 dB with 23 dBm power class |
| Downlink | OFDMA, 15 KHz tone spacing Turbo Code 16 QAM 1Rx | OFDMA 15 KHz tone spacing 1Rx | TDMA/FDMA, GMSK and 8PSK, 1Rx |
| Uplink | SC-FDMA 15 KHz tone spacing Turbo code, 16 QAM | SCFDMA 15 KHz tone spacing Turbo code | TDMA/FDMA, GMSK and 8PSK (optional) |
| Bandwidth | 1.08 MHz | 180 KHz | 200 kHz per channel, typical system bandwidth of 2.4 MHz |
| Peak rate (DL/UL) | DL and UL: 1 Mbps | DL: 50 kbps UL: 50 Kbps for multi-tone, 20 Kpbs for single tone | DL and UL: 70 kbps (GMSK) using 4 timeslots |
| Duplexing | FD & HD (type B), FDD & TDD | HD (type B), FDD | HD, FDD |
| Power saving | PSM, ext. I-DRX, C-DRX | PSM, ext I-DRX, C-DRX | PSM, ext. I-DRX |
| Power class | 23 dBm 20 dBm | 23 dBm | 33 dBm 23 dBm |

It is to be noted that commercial networks implemented in accordance with any of the LTE CAT-M1, CAT-NB1 and EC-GSM-IoT standards operate in the licensed spectrum of the radio-frequency spectrum (meaning that the frequency bands on which they operate are regulated by governmental regulatory bodies). Operation within the licensed spectrum requires operators to obtain a license or permit from a regulatory authority and to adhere to a set of technical, operational and behavioral rules, having the effect of potentially offering a higher quality of service (QOS) for delivery of communications between the MDAD 5 and the notification service 7 than may otherwise be obtained using networks operating in the unlicensed spectrum. It may therefore be advantageous to use such an available cellular network to communicate MDAD alert messages from the MDAD 5 to the notification service 7. However, it is to be understood that in other embodiments, it may be suitable or advantageous to use a LPWA network operating in an unlicensed frequency band of the radiofrequency spectrum. Examples of such networks may include, but are not limited to, LoRa, SigFox, etc. Furthermore, while a preferred embodiment of the MDAD is battery powered and therefore to conserve power connects to the notification service 7 via a LPWAN, in alternative embodiments where power consumption is not at issue for the MDAD, the MDAD may be implemented using a transmission module that allows it to transmit its alert messages via any wireless or wired network (including, but not limited to, LPWANs, LANs, WANs, WiFi Access Points, etc.) using an appropriate corresponding transmission protocol. For example, if the MDAD is not positioned in a remote location and has access to a Wi-Fi Access Point, the MDAD could be configured to include a WiFi transmission module and to send its alert messages to the notification service 7 by connecting to the Internet via a local WiFi Access Point. Similarly, if WiFi is not available but a cellular service (that is not an LPWAN) is available, the MDAD 5 could include transmission module that can communicate with the available cellular service (which may not be an LPWAN) and could then transmit its alert messages via that cellular service.

In an embodiment, the MDAD 300 further includes a low-power low- to mid-range transceiver or receiver (collectively, referred to as "transceiver") which can receive messages from one or more remote sensors. In an embodiment, the transceiver comprises a 433 MHz transceiver that listens for messages sent from remote sensor devices within distance of its operational range (e.g., within approximately 100 meters). In an embodiment, to conserve power, the transceiver is active or "wakes up" periodically (for example, every second or every few seconds) to listen for a message from a remote sensor unit. The remote sensor unit may be configured to transmit for a few times longer than the period the transceiver wake period, so that the MDAD is guaranteed to be in a wake period at least once during the sensor transmission period. In order to conserve battery life, both the transceiver of the MDAD and the sensor unit automatically go into a low-power mode when not transmitting or when not in a wake period. Further to conserve power, the transceiver component of the MDAD and the components of the sensor unit each comprises a low-power electronic component.

In an embodiment, the sensor(s) 406 comprise an accelerometer such as a low-power MEMS accelerometer previously discussed, and the MDAD/SAND 400 is attached to, embedded in, integrated into, or otherwise associated with an AED 102. The GNSS Receiver and processor 411 allow the controller 401 to collect, process and transmit location information from the GNSS to the Notification Service 300 for storage, monitoring and notification to notification recipients. Thus, if a MDAD/SAND 400 detects movement or another event sensed by a sensor 406a, 406b, 406n, 421a, 421b, 421m of the AED that it is monitoring, the Notification Service 300 can notify designated notification recipients of the following: (1) the movement or other sensed event was detected, and (2) the location of the AED. This information can help emergency personnel in finding an AED after it has moved or upon notification of other sensed events. The information can also assist emergency personnel in finding patients on which the AED has been used since once used, the AED is usually still with the patient by the time the emergency personnel arrives on the scene. Additionally, building and facilities management can be notified when an AED, which is typically installed in a semi-permanent location within a building, is tampered with (triggered by the vibration from tampering), thereby helping management to prevent theft and other unauthorized tampering.

It will be appreciated that the technologies, in particular the MDAD, SAND and Notification Service, may be implemented and used in many other applications. By way of example and not limitation, in an embodiment, the sensor unit may comprise one, or a combination of, the following sensors: an accelerometer, a microphone, a passive infrared (PIR) sensor, a reed switch, a camera, a liquid level sensor, a charge sensor, a load sensor, a voltage sensor, a resistance sensor, a capacitance sensor, a thermo sensor, a temperature sensor, a humidity sensor, a flex sensor, a pressure sensor, a chemical composition sensor, a light sensor, a UV Index sensor, a sound sensor, a wind sensor, a positioning sensor, a moisture sensor, etc. In an embodiment, a system includes a plurality of sensor units positioned in proximity (within receiver range) to the transceiver of a SAND. Such SAND includes program instructions to listen for sensor event alerts from sensor units 421 within its receiving range, identify the sensor sending a sensor event alert, decode such sensor event alert(s) and send one or more message alert(s) to the Notification Service to alert notification recipients to the occurrence of the sensor event using one of the designated notification delivery methods associated with the MDAD/SAND.

The mapping service discussed in connection with FIG. 9 may also be used to generate a map for display on a user's device 109. Locations of individual sensors 406 and the SAND may be overlaid on a map.

The MDAD may be used in a plurality of applications. In an embodiment, the SAND may be physically attached to a door, a window, a rodent or animal trap, a mailbox, a trashcan, a safe, a cabinet, a portable object such as a vehicle, a boat, a bicycle, a tractor, a generator, a beehive, a motor, or any object that one desires to monitor. Vibration caused by movement, tampering, falling, interference, or other interaction with the monitored object will generate a notification message to one or more designated notification that the monitored object has been moved, tampered or interfered with, fallen, or otherwise sensed a vibration or loud sound. In an embodiment, the SAND may be installed with the premises of a house, a garage, a shed, a remote building, etc. Loud sound caused by smoke and/or other sound-generating alarm systems may also generate a notification message to the one or more designated notification recipients associated with the SAND. Monitoring in this manner can be performed without requiring an external power supply or frequent battery replacement or recharging. The low-power unit can last 5-10 years using 3 conventional AAA or 2 AA batteries based on 2300 network connections (pings) at 2 pings per day.

Another advantage of the systems discussed herein, and in particular with respect to the SAND system with external sensors as discussed in connection with FIGS. 13-14 is that it allows end users to set up a monitoring and notification system on a modular basis. That is, an end user can install a SAND 400 in an environment, and then place remote sensor units 421a, 421b, 421m of the same or different types anywhere within the signal range of the SAND, and receive alerts if any one of the remote sensor units 421a, 421b, 421m alerts the SAND 400. The placement of the sensors 421a, 421b, 421m is completely up to the end user, and no sensor 421a, 421b, 421m is required to communicate with any other sensor 421a, 421b, 421m in the system. They need only transmit an alert using the sensor transceiver protocol that is recognized by the SAND 400, and the SAND 400 will pick up the alert and notify the Notification Service 123 to notify the notification recipients associated with the SAND 400. The modular monitoring system is easy to install because since the SAND 400 is equipped with a self-contained power source (i.e., a battery or solar panel/inverter) and does not require a WiFi or LAN access port. The SAND 400 and sensors 421a, 421b, 421m can be placed anywhere, including remote locations (so long as the LPWAN provides sufficient coverage to allow the SAND 400 to connect to the LPWAN. Modular, Do-It-Yourself simple to install and user-configurable monitoring system design, Always-On, Long-Lasting, self-contained—all these advantages over existing and prior art monitoring and notification systems.

It will further be appreciated that although the preferred embodiment uses an LPWAN over which to transmit alert messages, in other embodiments, the MDAD 105 and/or SAND 400 may additionally or instead be equipped with a WiFi modem to transmit the messages to the nearest WiFi access port and from there onto the Internet to the Notification Service.

What is claimed is:

1. An automated external defibrillator (AED) monitoring service, comprising:
a computer accessible via a network, the computer comprising at least one computer processor and computer readable storage memory, the storage memory storing program instructions which, when executed by the at least one computer processor, implements performance by the computer of:
receiving an alert message from a remote automated external defibrillator (AED) monitoring device, the receipt of the alert message initiating a sequence of communications between the remote AED monitoring device and the monitoring service, the remote AED monitoring device arranged to monitor a remote AED system, the alert message generated upon detection by the remote AED monitoring device of a sensed event at the AED monitoring device, the alert message comprising information related to identification of the monitored remote AED system and the sensed event;
extracting and processing the identification information to extract an identifier associated with the remote AED monitoring device;
extracting and processing the sensed event information to determine an event associated with the sensed event information;
generating a notification message indicating occurrence of the determined event at the monitored remote AED associated with the extracted remote AED monitoring device identifier;
retrieving from an electronic database an electronic delivery address associated with the extracted remote AED monitoring device identifier and a corresponding electronic delivery service identifier associated with the retrieved electronic delivery address; and sending the alert notification message to the retrieved electronic delivery address using an electronic delivery service identified by the retrieved electronic delivery service identifier; retrieving from the electronic database control information associated with the remote AED monitoring device identifier;
based on the retrieved control information, determining whether any intercommunication actions with the remote AED monitoring device are required, the intercommunication actions comprising one or more of: getting data from the remote AED monitoring device, sending data to the remote AED monitoring device, or configuring operational control of the remote AED monitoring device;
performing said determined required intercommunication actions, if any, with the remote AED monitoring device; and
signaling the remote AED monitoring device to place itself into a low-power mode; wherein the service can communicate with the remote AED monitoring device only upon initiation of communications by the remote AED monitoring device,
wherein the one or more actions comprises disabling a pause control feature at the remote AED monitoring device by sending instructions to the remote AED monitoring device instructing the remote AED monitoring device to enable sending of alert messages to the monitoring service, and wherein instructions instructing the remote AED monitoring device to enable sending of alert messages to the monitoring service can only be sent to the remote AED monitoring device during a communications sequence initiated by the remote AED monitoring device.

2. The AED monitoring service of claim 1, wherein the remote AED monitoring device exits the low-power mode only upon detection by the remote AED monitoring device of one or more predefined sensed events.

3. The AED monitoring service of claim 2, wherein the remote AED monitoring device exits the low-power mode additionally only upon passing of a predetermined amount of time since a last communication with the monitoring service to send a status message to the service.

4. The AED monitoring service of claim 1, the program instructions further implementing:
retrieving from the electronic database all electronic delivery addresses and corresponding electronic delivery service identifiers associated with the remote AED monitoring device identifier; and
sending the alert notification message to all the retrieved electronic delivery addresses using respective electronic delivery services associated with the respective retrieved electronic delivery addresses.

5. The AED monitoring service of claim 1, the program instructions further implementing:
receiving, from a remote user device that is independent of the remote AED monitoring device, a request to associate one or more electronic delivery addresses and corresponding electronic delivery services with the remote AED monitoring device;
storing, in the electronic database, each of the notification recipient electronic delivery addresses and identifiers associated with the respective corresponding electronic delivery services; and
associating, in the electronic database, the stored respective notification recipient electronic delivery addresses and corresponding electronic delivery service identifiers with the remote AED monitoring device.

6. The AED monitoring service of claim 5, wherein the monitoring service supports storing a plurality of different electronic delivery addresses and corresponding electronic delivery service identifiers in the electronic database in association with the remote AED monitoring device identifier.

7. The AED monitoring service of claim 6, wherein the program instructions further implement:
retrieving from the electronic database all the electronic delivery addresses and corresponding electronic delivery service identifiers associated the AED monitoring device identifier; and
sending the alert notification message to each of the retrieved electronic delivery addresses using respective electronic delivery services associated with each of the retrieved corresponding electronic delivery service identifiers.

8. The AED monitoring service of claim 1, the program instructions further implementing:
receiving, from a remote user device that is independent of the remote AED monitoring device, a request to set device configuration and control information associated with the remote AED monitoring device;
setting in the electronic database one or more configuration or control settings associated with the remote AED monitoring device corresponding to the device configuration and control information from the received request;

wherein the determined actions performed by the computer are based on the set configuration or control settings stored in the electronic database as associated with the remote AED monitoring device.

9. The AED monitoring service of claim 1, wherein the one or more actions comprises enabling a pause control feature at the remote AED monitoring device by sending instructions to the remote AED monitoring device instructing the remote AED monitoring device to pause sending of alert messages to the monitoring service for a predetermined amount of time.

10. The AED monitoring service of claim 9, wherein the remote AED monitoring device comprises a timer and the instructions sent by the remote AED monitoring device comprise a parameter used by the remote AED monitoring device to program the timer to count time corresponding to the predetermined amount of time.

11. The AED monitoring service of claim 1, the alert message further comprising information related to geo-location of the remote AED monitoring device, the program instructions further implementing:
  processing the location information from the alert message to extract the geo-location of the of the remote AED monitoring device, and
  incorporating the extracted geo-location into the alert notification message sent to the notification recipient.

12. The AED monitoring service of claim 1, the program instructions further implementing:
  receiving, from a remote user device that is independent of the remote AED monitoring device, a request to associate the remote AED monitoring device with a location;
  receiving from the remote user device electronic location information; storing the electronic location information in the electronic database; and
  associating the stored electronic location information with the remote AED monitoring device.

13. The AED monitoring service of claim 12, wherein the electronic location information comprises a user-identifiable location provided by a user of the remote user device.

14. The AED monitoring service of claim 12, wherein the electronic location information comprises geo-location data retrieved by a geo-location retrieval instructions executing on the remote user device, the geo-location retrieval instructions retrieving the location of the remote user device from a remote positioning system using a modem local to the remote user device that communicates with the remote positioning system.

15. The AED monitoring service of claim 1, wherein the retrieved electronic delivery service identifier identifies an email service.

16. The AED monitoring service of claim 1, wherein the retrieved electronic delivery service identifier identifies an electronic text service.

17. The AED monitoring service of claim 1, wherein the retrieved electronic delivery service identifier identifies an in-app push monitoring service.

18. The AED monitoring service of claim 1, wherein the sensed event comprises detection, by a sensor connected to the remote AED monitoring device, of a predetermined condition.

19. The AED monitoring service of claim 18, wherein the sensor comprises an accelerometer.

20. The AED monitoring service of claim 18, wherein the sensor comprises a passive infrared (PIR) sensor.

21. The AED monitoring service of claim 18, wherein the sensor comprises a microphone.

22. The AED monitoring service of claim 18, wherein the sensor comprises a capacitance sensor.

23. The AED monitoring service of claim 18, wherein the sensor comprises a reed switch.

* * * * *